(12) United States Patent
Ren et al.

(10) Patent No.: US 10,731,135 B2
(45) Date of Patent: Aug. 4, 2020

(54) REGENERATION OF A FUNCTIONAL PULMONARY VASCULAR BED

(71) Applicant: The General Hospital Corporation, Boston, MA (US)

(72) Inventors: Xi Ren, Malden, MA (US); Harald C. Ott, Wenham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/261,683

(22) Filed: Sep. 9, 2016

(65) Prior Publication Data

US 2017/0073645 A1    Mar. 16, 2017

Related U.S. Application Data

(60) Provisional application No. 62/217,615, filed on Sep. 11, 2015.

(51) Int. Cl.
| | |
|---|---|
| *C12N 5/00* | (2006.01) |
| *C12N 5/02* | (2006.01) |
| *A61K 35/32* | (2015.01) |
| *C07K 14/00* | (2006.01) |
| *C12N 5/071* | (2010.01) |
| *C12M 3/00* | (2006.01) |
| *C12M 1/36* | (2006.01) |
| *C12M 1/12* | (2006.01) |
| *C07K 14/475* | (2006.01) |

(52) U.S. Cl.
CPC .......... *C12N 5/0697* (2013.01); *C12M 21/08* (2013.01); *C12M 25/14* (2013.01); *C12M 41/48* (2013.01); *C12N 5/0688* (2013.01); *C07K 14/475* (2013.01); *C12N 2500/02* (2013.01); *C12N 2500/25* (2013.01); *C12N 2501/01* (2013.01); *C12N 2501/11* (2013.01); *C12N 2501/115* (2013.01); *C12N 2501/135* (2013.01); *C12N 2501/15* (2013.01); *C12N 2501/155* (2013.01); *C12N 2501/165* (2013.01); *C12N 2501/17* (2013.01); *C12N 2501/39* (2013.01); *C12N 2501/415* (2013.01); *C12N 2502/1388* (2013.01); *C12N 2502/27* (2013.01); *C12N 2502/28* (2013.01); *C12N 2506/45* (2013.01); *C12N 2533/92* (2013.01)

(58) Field of Classification Search
CPC .............. C12N 5/0688; C12N 5/0697; C12N 2501/10; C12N 2502/27; C12N 2502/28; C12N 2502/1352; C12M 25/14; C12M 21/08; C07K 14/475
USPC .......... 435/373, 375, 395; 424/574; 530/399
See application file for complete search history.

(56) References Cited

U.S. PATENT DOCUMENTS

| | | | |
|---|---|---|---|
| 8,470,520 | B2 | 1/2013 | Ott et al. |
| 9,005,885 | B2 | 4/2015 | Ott |
| 9,974,814 | B2 | 5/2018 | Katane et al. |
| 10,105,208 | B2 | 10/2018 | Tranquillo et al. |
| 10,111,740 | B2 | 10/2018 | Tranquillo et al. |
| 10,213,525 | B2 | 2/2019 | Ross |
| 10,220,056 | B2 | 3/2019 | Ott et al. |
| 10,233,420 | B2 | 3/2019 | Taylor et al. |
| 2003/0087428 | A1 | 5/2003 | Wolfinbarger et al. |
| 2005/0256588 | A1 | 11/2005 | Sawa et al. |
| 2007/0244568 | A1 | 10/2007 | Matsuda et al. |
| 2009/0142836 | A1 | 6/2009 | Wang et al. |
| 2012/0064537 | A1 | 3/2012 | Ross |
| 2012/0141439 | A1 | 6/2012 | Ott |
| 2012/0183944 | A1 | 7/2012 | Taylor et al. |
| 2013/0109088 | A1 | 5/2013 | Ott et al. |
| 2013/0337560 | A1 | 12/2013 | Ross et al. |
| 2014/0273220 | A1 | 9/2014 | Gerecht |
| 2016/0030637 | A1 | 2/2016 | Ross et al. |
| 2018/0064848 | A1 | 3/2018 | Ross et al. |
| 2018/0325650 | A1 | 11/2018 | Tranquillo et al. |
| 2019/0284523 | A1 | 9/2019 | Taylor et al. |
| 2019/0343877 | A1 | 11/2019 | Ott et al. |

FOREIGN PATENT DOCUMENTS

| | | |
|---|---|---|
| EP | 2484754 | 8/2012 |
| WO | WO 2014/110135 | 7/2014 |
| WO | WO 2014/168264 | 10/2014 |
| WO | WO 2014 /200340 | 12/2014 |
| WO | WO 2015/119642 | 8/2015 |
| WO | WO 2015/138999 | 9/2015 |

OTHER PUBLICATIONS

Ludlow et al., Jan. 29, 2015, US 20150030657 A1.*
Pickering et al., 2011, US 20110104132 A1.*
Rapoport et al., 2009, US 20090227026 A1.*
Ott, Harald, 2012, US 20120141439 A1.*
Ott, Harold C., 2017, US 20170015963 A1, effective fling date, Mar. 14, 2014.*
Au et al., Bone marrow-derived mesenchymal stem cells facilitate engineering of long-lasting functional vasculature, Blood, May 2008, 111: 4551-4558.

(Continued)

*Primary Examiner* — Shin Lin Chen

(74) *Attorney, Agent, or Firm* — Fish & Richardson P.C.

(57) ABSTRACT

A method for vascular regeneration comprises delivering endothelial cells to a lung scaffold, delivering perivascular cells to the lung scaffold, and providing a multiphase culture program to the scaffold. The multiphase culture program comprises a first phase including delivering an angiogenic medium, e.g., having 40-100 ng/ml of pro-angiogenic factors, and a second phase including delivering a stabilization medium, e.g., having 0.5-2% of serum and 1-20 ng/ml of angiogenic factors.

6 Claims, 13 Drawing Sheets

(56) References Cited

OTHER PUBLICATIONS

Boasquevisque et al., "Surgical Techniques: Lung Transplant and Lung Volume Reduction," Proceedings of the American Thoracic Society, Jan. 2009, 6:66-78.

Camargo et al., "Surgical maneuvers for the management of bronchial complications in lung transplantation," Eur J Cardiothorac Surg. Jun. 2008, 34: 1206-1209.

Desai and Cardoso, "Growth factors in lung development and disease: friends or foe?," Respire. Res., 2002, 3:2.

Gaissert and Patterson, "Surgical Techniques of Single and Bilateral Lung Transplantation," The Transplantation and Replacement of Thoracic Organs, 1996, 457-463.

Gilbert et al., "Decellularization of tissues and organs," Biomaterials, 2006, 27(9) :3675-83.

Gilpin et al., "Perfusion decellularization of 15 human and porcine lungs: Bringing the matrix to clinical scale," Journal of Heart and Lung Transplantation, Mar. 2014, 33: 298-308.

Guyette et al, "Perfusion decellularization of whole organs," Nat Protoc, 2014, 9: 1451-1468.

International Search Report and Written Opinion in International Application No. PCT/US2016/051049, dated Dec. 12, 2016, 13 pages.

James et al., "Expansion and maintenance of human embryonic stem cell-derived endothelial cells by TGFbeta inhibition is Id1 dependent," Nat Biotechnol, Feb. 2010, 28: 161-166.

Liao et al, "Effects of Decellularization on the Mechanical and Structural Properties of the Porcine Aortic Valve Leaflet," Biomaterials, Mar. 2008, 29(8): 1065-74.

Maghsoudlou et al., "Preservation of micro-architecture and angiogenic potential in a pulmonary acellular matrix obtained using intermittent intra-tracheal flow of detergent enzymatic treatment," Biomaterials, Sep. 2013, 34(28):6638-48.

Melero-Martin et al., "In vivo vasculogenic potential of human blood-derived endothelial progenitor cells," Blood, Jun. 2007, 109: 4761-4768.

Nichols et al., "Production and assessment of decellularized pig and human lung scaffolds," Tissue Eng: Part A., Sep. 2013, 19 (17-18):2045-62.

O'Neill et al., "Decellularization of human and porcine lung tissues for pulmonary tissue engineering," Ann Thorac Surg, Sep. 2013, 96(3): 1046-55.

Ott et al., "Regeneration and orthotopic transplantation of a bioartificial lung," Nat Med, Aug. 2010,16(8):927-33.

Petersen et al., "Tissue-Engineered Lungs for in Vivo Implantation," Science, Jul. 2010, 329: 538-541.

Ren et al., "Engineering pulmonary vasculature in decellularized rat and human lungs," Nature Biotechnology, Oct. 2015, 33: 1097-1102.

Song and Ott, "Bioartificial lung engineering," Am J Transplant, Feb. 2012,12(2):283-8.

Teebken et al., "Tissue Engineering of Vascular Grafts: Human Cell Seeding of Decellularised Porcine Matrix," Eur. J Vase. Endovasc. Surg., 2000, 19:381-86.

Venuta et al., "Evolving Techniques and Perspectives in Lung Transplantation," Transplantation Proceedings, Jul.-Aug. 2005, 37(6):2682-2683.

Yang and Conte, "Finer techniques in lung transplantation," Transplantation Proceedings, Nov. 2000, 32(7):1521-1522.

Yoshida et al., "Surgical Technique of Experimental Lung Transplantation in Rabbits," Ann Thorac Cardiovasc Surg., 2005, 11(1):7-11.

U.S. Appl. No. 16/243,592, filed Jan. 9, 2019.

* cited by examiner

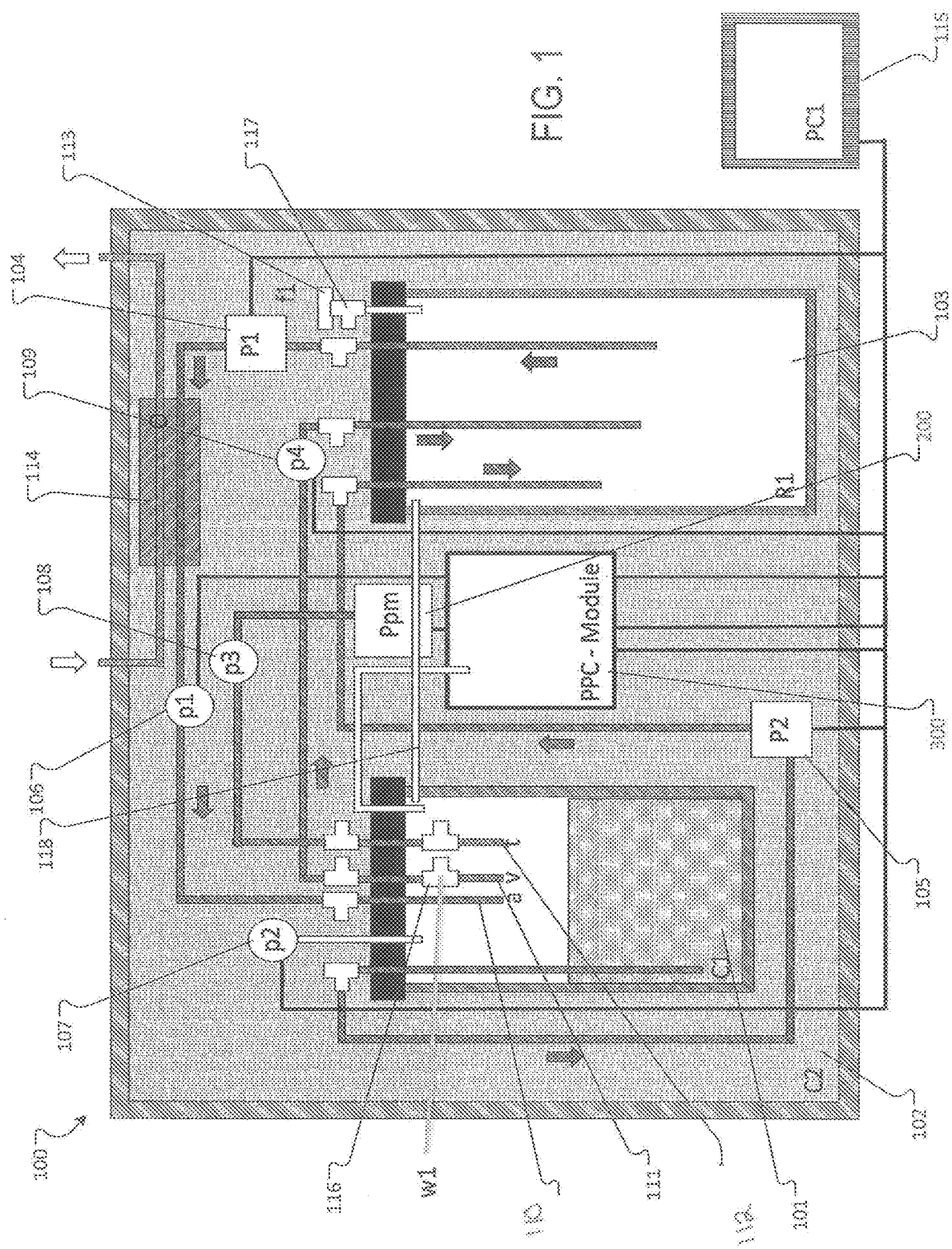

FIG. 7D
FIG. 7E
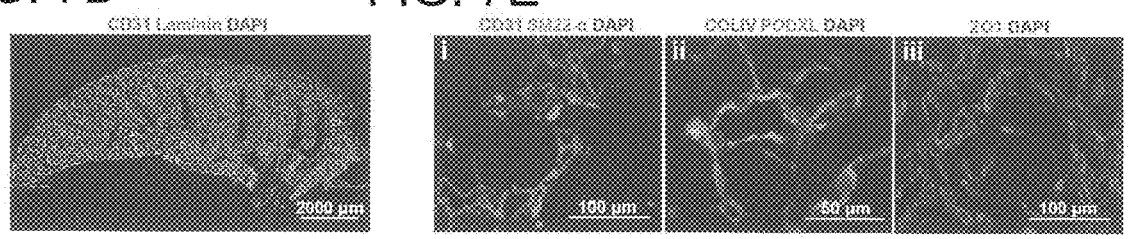
FIG. 7G
FIG. 7H
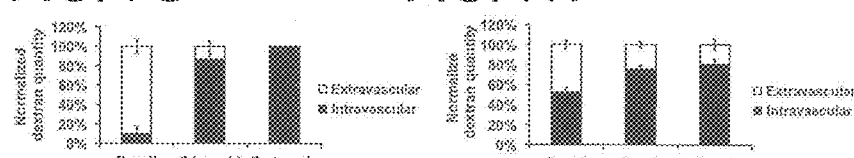

FIG. 7I
FIG. 7J
FIG. 7K
FIG. 7L
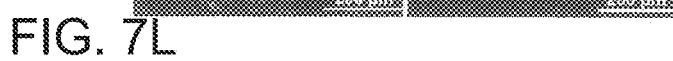

FIG. 12A
FIG. 12B
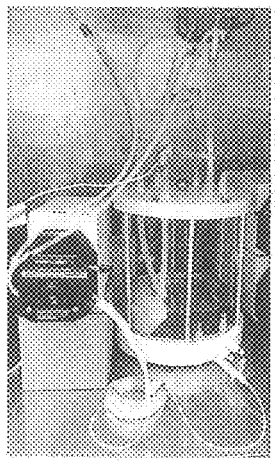
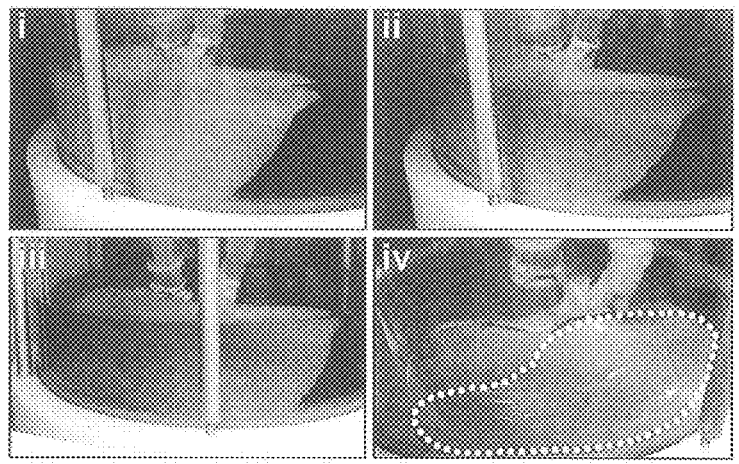
FIG. 12C
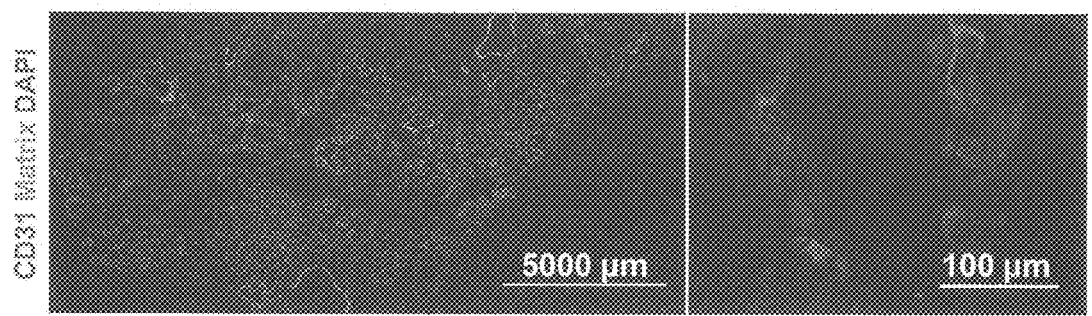
FIG. 12D
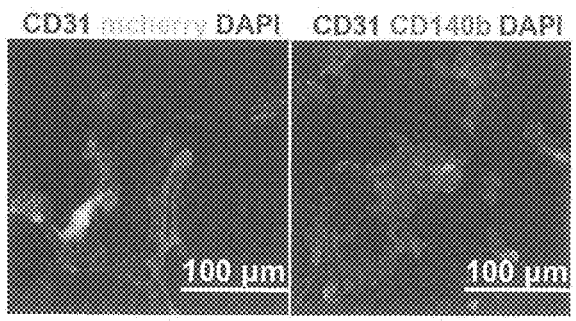
FIG. 12E
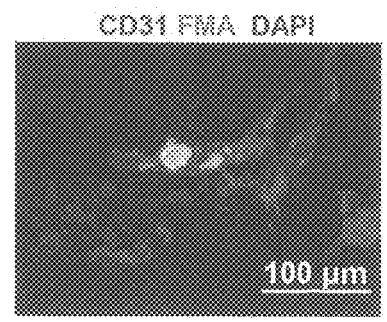

REGENERATION OF A FUNCTIONAL PULMONARY VASCULAR BED

PRIORITY

This application claims the benefit of U.S. Provisional Application No. 62/217,615, filed Sep. 11, 2015, the entire contents of which are hereby incorporated by reference.

TECHNICAL FIELD

This disclosure relates to the regeneration of a functional pulmonary vascular bed.

BACKGROUND

Lung transplantation is an effective treatment option for patients suffering from end-stage lung disease. However, donor numbers do not meet the increasing demand, while effects of chronic immunosuppression and rejection limit long-term outcomes. Typical wait time for a lung transplant can be two years or more, resulting in a 30% mortality rate for those on the waiting list.

SUMMARY

The present disclosure is based, at least in part, on the development of devices (e.g., bioreactors) and methods capable of regenerating a functional pulmonary vascular bed by delivering cells and repopulating the vascular compartment of an acellular lung scaffold with endothelial and perivascular cells and maturing the pulmonary vascular bed using a multiphase culture program. Implementations can include one or more of the following features.

In a first aspect, provided herein are methods for vascular regeneration comprising delivering endothelial cells to a lung scaffold; delivering perivascular cells to the lung scaffold; and providing a multiphase culture program to the scaffold, the multiphase culture program comprising: a first phase including delivering an angiogenic medium having 40-100 ng/ml of pro-angiogenic factors, and a second phase including delivering a stabilization medium having 0.5-2% of serum and 1-20 ng/ml of angiogenic factors.

In some embodiments, the pro-angiogenic factors include at least one or more, e.g., two, three, four, or all five of recombinant human vascular endothelia growth factor, basic fibroblast growth factor, angiopoietin 1, epidermal growth factor, and platelet-derived growth factor VEGF, bFGF, ANG1, EGF and PDGF).

In some embodiments, the stabilization medium includes at least one of forskolin and/or hydrocortisone.

In some embodiments, the methods include maintaining the lung scaffold in a bioreactor surrounding the lung scaffold, the bioreactor comprising a tracheal line, an arterial line, and a venous line. In some embodiments, the lung scaffold comprises an airway and vasculature, and the method includes connecting the airway to the tracheal line; connecting the lung scaffold to the arterial line and to the venous line; and seeding the lung scaffold with cells over the arterial line and the venous line.

Also provided herein are methods for vascular regeneration that can include delivering HUVECs and perivascular supporting hMSCs to a lung scaffold; delivering an angiogenic medium to the lung scaffold during a first phase; and delivering a stabilization medium to the lung scaffold during a second phase.

In some embodiments, the methods include maintaining the lung scaffold in a bioreactor surrounding the lung scaffold, the bioreactor comprising a tracheal line, an arterial line, and a venous line, wherein the HUVECs and perivascular supporting hMSCs are delivered through the arterial line and the venous line.

Further, provided herein are methods for differentiating endothelial and perivascular cells from human induced pluripotent stem cells (hiPSCs). The methods include culturing the hiPSCs in the presence of at least one GSK3 inhibitor; culturing the hiPSCs in the presence of a complete differentiating medium; culturing the hiPSCs with the differentiating medium supplemented with a TGF-β1 inhibitor; and separating hiPSC-derived perivascular progenitor cells (hiPSC-PPCs) and hiPSC-derived endothelial cells (hiPSC-ECs).

In some embodiments, the at least one GSK3 inhibitor is CHIR99021. In some embodiments, the at least one TGF-β1 inhibitor is SB431542.

In some embodiments, the methods include maintaining hypoxic culture conditions of 4% or less of $O_2$.

In some embodiments, the methods include measuring a plateau in an increase of endothelial coverage defined by CD31 and VE-cadherin expression to indicate sufficient vascular and the end of a first phase of culture.

Various embodiments provide apparatuses and systems for implementing methods described herein. In some implementations the apparatuses and/or systems may include a control system including a computer control for implementing the methods described. The control system can include a non-transitory computer-readable storage medium coupled to one or more processors and having instructions stored thereon which, when executed by the one or more processors, cause the one or more processors to perform operations for vascular regeneration according to anyone of the preceding implementations or embodiments described herein.

As used herein, a "functional" lung tissue performs most or all of the functions of a normal healthy lung, which include allowing for transportation of oxygen from the air into the bloodstream, releasing of carbon dioxide from the bloodstream into the air, humidifying inhaled air, producing surfactant to decrease surface tension in the alveoli, and producing and transporting mucus to remove inhaled particulate matter from the distal to the proximal airway. In some embodiments, "functional" lung tissue will, at a minimum, allow for transportation of oxygen from the air into the bloodstream and release of carbon dioxide from the bloodstream into the air.

As used herein, the terms "decellularized" and "acellular" are used or defined as the complete or near complete absence of detectable intracellular matter, endothelial cells, epithelial cells, and nuclei in histologic sections using standard histological staining procedures. Preferably, but not necessarily, residual cell debris also has been removed from the decellularized organ or tissue.

In some implementations, the compositions, devices, and methods described herein may have particular advantages to improve vascular regeneration of native extracellular matrix scaffolds. For example, certain implementations may provide method to deliver cells, such as endothelial cells or progenitor cells, through both the pulmonary artery and pulmonary vein, which can result in doubled endothelial coverage from that obtained from conventional arterial endothelial delivery methods, while also providing a homogenous endothelial coverage throughout the lung. In other examples, certain implementations may provide a two-phase organ culture program that can include an angiogenic medium followed by a stabilization medium. This multi-phase combination can help to first promote efficient endothelial remodeling and then promote vascular stabilization and barrier function functionality. The two-phase culture program can be combined with patient-derived cell sources to generate functional pulmonary vasculature using clinically relevant cell sources.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and from the following claims.

DESCRIPTION OF DRAWINGS

FIG. 1 is a schematic diagram of an exemplary lung bioreactor including a negative pressure wet ventilation system with a perfusion system and with a pneumatic pressure control module as shown in FIG. 3.

FIG. 7D is a representative stitched image showing endothelial coverage of a HUVEC-hMSC regenerated lung lobe after two-phase culture (CD31, red; Laminin, green; DAPI, blue).

FIG. 7E is an image characterizing HUVEC-hMSC regenerated lungs at the end of two-phase culture. (i) Interconnected vascular network structures formed by endothelial cells (CD31, red) with individual hMSCs (SM22α, green) adhering to the network. (ii) Establishment of apical-basal polarity shown by localization of PODXL (green) on the luminal surface and ColIV (red) on the basement surface. (iii) Establishment of tight junctions between endothelial cells shown by enrichment of cell border-associated ZO-1 (red).

FIG. 7G is a graph showing a quantification of dextran quantities in the intravascular (PV fluid) and extravascular (fluids from lung periphery and trachea including BAL) compartments after the in vitro perfusion and BAL assay on freshly isolated cadaveric lungs (Cadaveric), lungs after 6-hour cold ischemia (6-hr-cold ischemia) and acellular lungs (Decell).

FIG. 7H is a graph showing a quantification of dextran quantities in the intravascular and extravascular compartments after the in vitro perfusion and BAL assay on HUVEC-hMSC regenerated lungs on day 3, 6, and 8 of culture FIG. 7I is a graph showing daily PA pressure measurement of HUVEC-hMSC regenerated lungs (normalized to the pressure values on day 1).

FIG. 7J is a graph showing wet/dry ratios of accessory lobes from freshly isolated cadaveric lungs (Cadaveric), lungs after 6-hour cold ischemia (6-hr-cold ischemia), acellular lungs (Decell) and HUVEC-hMSC regenerated lungs at the end of two-phase culture (Regen).

FIG. 7K is an image showing orthotopic transplantation of HUVEC-hMSC regenerated lungs. Representative pictures showed a regenerated left lung graft after anastomosis of the PA and PV, before (left panel) and after (right panel) re-perfusion.

FIG. 7L is an image showing fluorescence microangiography (FMA) of regenerated left lung grafts 3 days after transplantation, showing 0.2-µm microspheres (FMA, green) perfused through the regenerated vascular network (CD31, purple).

FIG. 12A is an image of a bioreactor setup for vascular regeneration in acellular human lung lobes allowing endothelial delivery and perfusion through both the PA and PV.

FIG. 12B is a series of representative images of the regenerated human lung lobe during culture (i), right after (ii), during (iii) and at the end of (iv) resazurin perfusion. The dotted line indicated the recellularized area highlighted by resazurin metabolism (iv).

FIG. 12C is a representative stitched image of an hiPSC regenerated human lung lobe after two-phase culture (CD31, purple; matrix autofluorescence, green; DAPI, blue).

FIG. 12D is an image showing the presence of individual hiPSC-PPCs (mCherry, yellow, left panel; CD140b, green, right panel) adhering to the endothelial network formed by hiPSC-ECs (CD31, purple).

FIG. 12E is an image showing the fluorescence microangiography (FMA) of an hiPSC regenerated human lung lobe, showing 0.2-µm microspheres (FMA, green) perfused through the regenerated vascular network (CD31, purple).

DETAILED DESCRIPTION

Figure 2A:
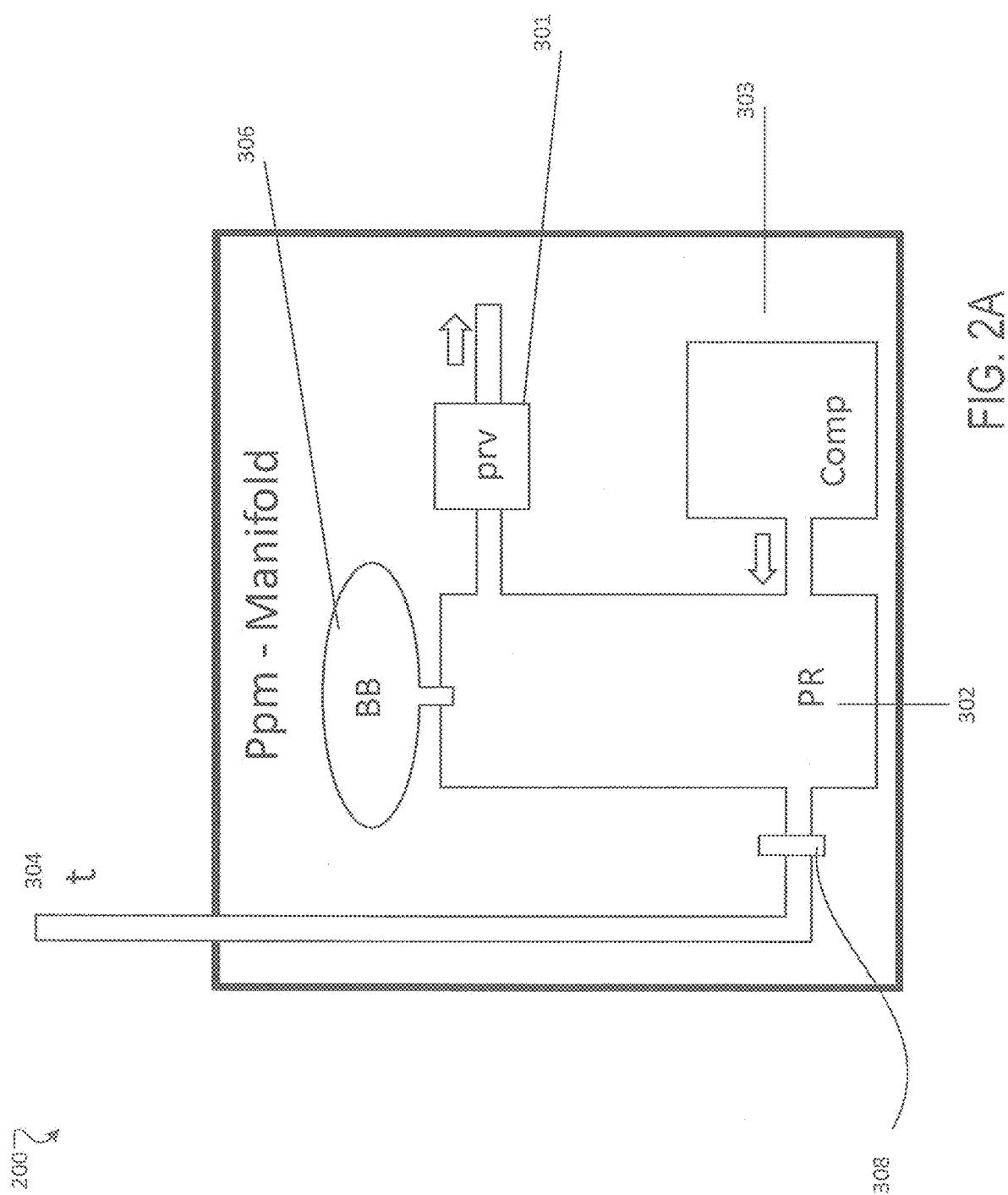
FIGS. 2A and 2B are schematic diagrams of an exemplary positive pressure manifold represented in FIG. 1.

This document relates to methods and materials involved in regenerating a pulmonary vascular bed. Described herein is the development of devices (e.g., bioreactors) and methods capable of regenerating a functional pulmonary vascular bed by delivering cells and repopulating the vascular compartment of an acellular lung scaffold with endothelial and perivascular cells and maturing the pulmonary vascular bed using a multiphase culture program.

Pulmonary vascular beds of bioartificial lung tissues (e.g., whole organs or portions thereof) can be generated or regenerated according to the methods provided herein. In some embodiments, the methods comprise transplanting a bioartificial lung tissue as provided herein to a subject (e.g., a human patient) in need thereof. In some embodiments, a bioartificial lung tissue is transplanted to the site of diseased or damage tissue. For example, bioartificial lung tissues can be transplanted into the chest cavity of a subject in place of (or in conjunction with) a non-functioning or poorly-functioning lung; methods for performing lung transplantation are known in the art, see, e.g., Boasquevisque et al., Surgical Techniques: Lung Transplant and Lung Volume Reduction, *Proceedings of the American Thoracic Society* 6:66-78 (2009); Camargo et al., Surgical maneuvers for the management of bronchial complications in lung transplantation, *Eur J Cardiothorac Surg* 2008; 34:1206-1209 (2008); Yoshida et al., "Surgical Technique of Experimental Lung Transplantation in Rabbits," *Ann Thorac Cardiovasc Surg.* 11(1):7-11 (2005); Venuta et al., Evolving Techniques and Perspectives in Lung Transplantation, Transplantation Proceedings 37(6):

2682-2683 (2005); Yang and Conte, *Transplantation Proceedings* 32(7):1521-1522 (2000); Gaissert and Patterson, Surgical Techniques of Single and Bilateral Lung Transplantation in The Transplantation and Replacement of Thoracic Organs, 2d ed. Springer Netherlands (1996).

The methods can include transplanting a bioartificial lung or portion thereof as provided herein during a surgical procedure to partially or completely remove a subject's lung and/or during a lung resection. The methods can also include harvesting a lung or a portion thereof from a live donor or cadaver and preserving or regenerating the lung in a bioreactor described herein. In some cases, the methods provided herein can be used to replace or supplement lung tissue and function in a subject, e.g., a human or animal subject.

Decellularized Tissue/Organ Matrices

There are various methods and materials for preparing a decellularized lung tissue matrix. Any appropriate materials can be used to prepare such a matrix. In certain embodiments, a tissue matrix can be an acellular tissue scaffold developed from decellularized lung tissue. For example, tissue such as a human lung, e.g., one or a pair of human lungs or portions thereof, e.g., human, porcine, bovine, primate, or ovine cadaveric lungs or portions thereof, can be decellularized by an appropriate method to remove native cells from the tissue while maintaining morphological integrity and vasculature of the tissue or tissue portion and preserving extracellular matrix (ECM) proteins. Methods for decellularizing mammalian lung tissues are described, e.g., in O'Neill J D et al., Decellularization of human and porcine lung tissues for pulmonary tissue engineering. *Ann Thorac Surg.* 2013 September; 96(3):1046-55; Nichols J E et al., Production and assessment of decellularized pig and human lung scaffolds, *Tissue Eng Part A.* 2013 September; 19(17-18):2045-62; Gilpin S E et al., Perfusion decellularization of human and porcine lungs: Bringing the matrix to clinical scale. *Journal of Heart and Lung Transplantation*. In press; Song J J et al., Bioartificial lung engineering. *Am J Transplant*. 2012 February; 12(2):283-8; Guyette, J. P. et al. Perfusion decellularization of whole organs. *Nat Protoc* 9, 1451-1468 (2014), and Ott H C et al., Regeneration and orthotopic transplantation of a bioartificial lung. *Nat Med*. 2010 August; 16(8):927-33. Exemplary decellularization methods can include subjecting tissue (e.g., lung tissue) to repeated freeze-thaw cycles, for example using liquid nitrogen. In other cases, a tissue can be subjected to an anionic or ionic cellular disruption medium such as sodium dodecyl sulfate (SDS), polyethylene glycol (PEG), or TritonX. The tissue can also be treated with a nuclease solution (e.g., ribonuclease, deoxyribonuclease) and washed in sterile phosphate buffered saline with mild agitation. Exemplary methods are known in the art e.g., O'Neill J D et al., Decellularization of human and porcine lung tissues for pulmonary tissue engineering. *Ann Thorac Surg.* 2013 September; 96(3):1046-55. In some cases, decellularization can be performed by flushing the vessels, ducts, and/or cavities of the organ or tissue using methods and materials known in the art. For example, as described in Maghsoudlou P et al., Preservation of micro-architecture and angiogenic potential in a pulmonary acellular matrix obtained using intermittent intra-tracheal flow of detergent enzymatic treatment. *Biomaterials*. 2013 September; 34(28):6638-48. Following the flushing step, the organ or tissue can be perfused via the line with a cellular disruption medium as described above for example 1% SDS in deionized water. Perfusion through the tissue can be anterograde or retrograde, and directionality can be alternated to improve perfusion efficiency. Depending upon the size and weight of an organ or tissue and the particular anionic or ionic detergent(s) and concentration of anionic or ionic detergent(s) in the cellular disruption medium, a tissue generally is perfused from about 2 to about 12 hours per 10 grams of tissue with cellular disruption medium. Including washes, an organ may be perfused for up to about 12 to about 72 hours per 10 grams of tissue. Perfusion generally is adjusted to physiologic conditions including flow rate and pressure, e.g., pressure between 5-100 mmHg, and flow rate between 0.1-10 times the physiologic cardiac output of the source organism or individual.

In another exemplary method, a decellularization method includes perfusing a detergent, e.g., (1) 0.1% SDS (2) 2%, sodium deoxycholate (SDC), or (3) 8 mmol/liter (3)3-[(3-cholamidopropyl)dimethylammonio]-1-propanesulfonate (CHAPS) (pH12) detergent, through the pulmonary artery at a constant pressure of 30 cm $H_2O$. The protocol for all 3 detergents includes:

1. a 10-minute initial antegrade wash with phosphate-buffered saline (PBS),
2. detergent perfusion for the time required to visualize an opaque translucent matrix (indicative of decellularization) plus an additional 20% of that initial time (e.g., 70 minutes+ 14 minutes),
3. 15-minute deionized $H_2O$ wash, and
4. an additional 172-hour PBS wash with added antibiotics and antimycotics. This decellularization method, e.g., can include an additional wash of 1% Triton-X following the deionized $H_2O$. The SDC protocol can include a 0.1% Triton-X perfusion before SDC and a 1 mol/liter NaCl wash after SDC.

Similarly, porcine and human lung decellularization methods can include perfusion of a detergent or other decellularization agent though the pulmonary artery at constant pressure, followed by sequential washing with $H_2O$, 1% Triton-X solution, and PBS. Similar to rat lungs, decellularization can be deemed complete upon visual inspection and the appearance of an opaque translucent matrix. Variability in the starting organ, mainly due to extensiveness of pre-flushing during harvest and any resulting clots can contribute to the required length of perfusion. In general, the time of decellularization perfusion can vary e.g., from 4 to 7 days.

Decellularized tissue can consist essentially (e.g., at least: 85% pure, 90% pure, 92% pure, 95% pure, 96% pure, 97% pure, 98% pure, and 99% pure by weight) of the extracellular matrix (ECM) component of all or most regions of the tissue, including ECM components of the vascular tree. ECM components can include any or all of the following or any combination of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. In certain embodiments, decellularized lung tissue matrix retains an intact decellularized vasculature. Preserving a substantially intact decellularized vasculature enables connection of the tissue matrix to a subject's vascular system upon transplantation. In addition, a decellularized tissue matrix can be further treated with, for example, irradiation (e.g., UV, gamma) to reduce or eliminate the presence of any type of microorganism remaining on or in a decellularized tissue matrix.

Methods for obtaining decellularized tissue matrices using physical, chemical, and enzymatic means are known in the art, see, e.g., Liao et al, *Biomaterials* 29(8):1065-74 (2008); Gilbert et al., *Biomaterials* 27(9):3675-83 (2006);

Teebken et al., *Eur. J. Vasc. Endovasc. Surg.* 19:381-86 (2000). See also U.S. Pat. Publication Nos. 2009/0142836; 2005/0256588; 2007/0244568; and 2003/0087428.

Airway Organ Bioreactor Apparatus

Bioartificial lung tissues (e.g., whole organs or portions thereof) as described herein can be generated using bioreactors configured to provide a realistic environment conducive to lung tissue growth, preservation, repair, modification, or a combination thereof. An exemplary airway organ bioreactor is presented in FIGS. 1-3. Throughout the specification, a lung will be offered as an example of an organ or an airway organ. Other examples can include a portion of a lung that includes a hierarchal vasculature structure, e.g., a lobe or a segment. The exemplary bioreactor presented in FIGS. 1-3 is capable of supporting a harvested lung from a live donor or cadaver. Any of the bioreactors described herein can be configured to permit culture of a lung in a supine position.

Referring to FIG. 1, components of the bioreactor 100 include a lung chamber 101, an incubator chamber 102, a media reservoir 103, an arterial perfusion pump 104, a drainage pump 105, an arterial pressure sensor 106, a chamber pressure sensor 107, a tracheal pressure sensor 108, a venous pressure sensor 109, an arterial line 110, a venous line 111, a tracheal line 112, a sterile filter 113, an oxygenator 114, a control module 115, a venous valve 116, a filter occluder 117, an equilibration line 118, a pneumatic pressure control (PPC) module 300, and a positive pressure manifold (PPM) 200.

Within the lung chamber 101, the cell matrix is perfused antegradely with a cells and media to allow seeding of cells to grow in the lung matrix. The perfusion takes place through the arterial line 110 to the pulmonary artery and through the venous line 111 to the pulmonary vein. This configuration permits the cells and media to reach the capillary bed from both the arterial and venous sides and permits the media to diffuse through the acellular basement membrane and exit the matrix via the trachea or across the pleura.

The cells and/or media flow through the arterial line 110 and the venous line 111 through the pulmonary vasculature. To recirculate, the media passes through the oxygenator 114. The oxygenated media flows through the arterial perfusion pump 104. This pump is controlled by the control module 115 that controls the speed of the based on the pressure readings from the arterial pressure sensor 106 and the venous pressure sensor 109 respectively. Arterial and venous perfusion pressures can be modified based on the size and number of cells to optimize cell delivery. The control module 115 is also capable of recording data (e.g., resistance readings from arterial pressure sensor 106, and venous pressure sensor 109. The media completes the circuit, returning to the arterial line 110. During initial anterograde seeding, media diffuses through the lung matrix before it or as it reaches the capillary bed. To guide media through the scaffold, the positive pressure manifold 200 can modify the pressure within the lung. In some cases, retrograde seeding can be used.

After the decellularization of the lung, matrix is sufficient to withstand physiological conditions (e.g., vascular resistance increases due to the reendothelialization of the lung matrix) and the bioreactor 100 switches to anterograde perfusion. The vasculature resistance is measured by the arterial pressure sensor 106 over time. As the vascular system is populated, the diffusion across the vascular membrane decreases causing an increase in the pressure measured by the arterial sensor 106 (i.e., an increase in vascular resistance). In some examples, particles (e.g., microspheres) are perfused through the bioreactor 100 and their progress is monitored to determine the diffusion rate across the vascular membrane.

The bioreactor 100 combines a flow perfusion system and negative pressure ventilation. A lung matrix is placed in lung chamber 101. The flow perfusion system uses the arterial line 110 connected to the pulmonary artery of the lung. The media is aspirated from the media reservoir 103 and passes through the oxygenator 114. The oxygenator 114 exchanges air with the environment surrounding the incubator chamber 102. After passing through the oxygenator 114, arterial pressure sensor 106 records the arterial pressure and transmits this data to the control module 115. The arterial pressure reading then regulates the roller pump that pumps media from the reservoir to the pulmonary artery. The media then circulates out of the lung chamber 101 through an egress line and is pumped using the drainage pump 105 into the media reservoir 103. The drainage pump 105 is bi-directional and can be used to circulate media between the media reservoir 103 and the lung chamber 101. This recirculation also helps to maintain the correct pH in the lung chamber 101. The control module 115 controls the drainage pump 105, e.g., speed and/or direction, based on pressure readings recorded by the chamber pressure sensor 107. As the chamber pressure in lung chamber 101 fluctuates, liquid flows in and out of the tracheal line 112. Because the venous line 111 is open to the media reservoir 103, the venous pressure equilibrates to the chamber pressure thus preventing a transpulmonary pressure gradient that can cause fluid to flow from the artery into the tissue. By monitoring the chamber pressure and pumping accordingly, the media level in the lung chamber 101 can be maintained.

As shown in FIG. 1, the bioreactor 100 also includes the tracheal pressure sensor 108 and the venous pressure sensor 109. The tracheal pressure sensor 108 measures pressure within the airway (e.g., the trachea).

The bioreactor 100 can also use the venous pressure sensor 109 to actively monitor the media exchange rate between the venous line 111 and the media reservoir 103. The venous after load into the system is controlled by the level of the reservoir when venous valve 116 is closed, or by a resistance valve that can be attached to venous valve 116 if it is open position. For example, the venous valve 116 is generally in an open position. A low-pressure reading (e.g., <−5 mmHg) may trigger the venous valve 116 to close (e.g., automatically or by an operator) thus providing more venous backpressure to prevent post-capillary vascular collapse. If the pressure reading is high (e.g. >20 mm Hg, the venous valve 116 can open to reduce the venous afterload and minimize fluid shifts into the interstitial space and airways.

Still referring to FIG. 1, the pressure in the media chamber 103 is equilibrated with the ambient environment (e.g., the incubator chamber 102) through the sterile filter 113. This exchange also permits the exchange of gasses (e.g., carbon dioxide) between the incubator chamber 102 and the media reservoir 103, which helps maintain the appropriate pH values of the media in the system. The height of the media reservoir 103 may be adjusted relative to the height of the lung chamber 101. This causes a positive wet respiratory pressure and affects the tracheal airway pressure in relation to the lung. For example, the media reservoir 103 is set at 4 cm above the lung submerged in the media. This causes a positive airway pressure.

Generally, the pressure recorded by any of the sensors described herein is within physiological ranges depending on the organ cultured. For example, the arterial ranges may be a mean of 10-35 mmHg, the lung chamber 101 may be between a mean of −40 to 40 mmHg.

The pressure equilibration line 118 between the lung chamber 101 and the media reservoir 103 and the filter occluder 117 on the sterile filter 113 equalize pressures between the lung chamber 101 and the media reservoir 103. This ensures equal pressure across both chambers during all phases of the respiratory cycle. This modification can be applied to all bioreactors discussed herein, both small animal and large animal/human, and can be used in both positive and negative pressure ventilation modes and wet and dry ventilation modes. The introduction of this pressure equilibration, line 118 enables the creation of a bi-directional transpulmonary gradient. In other words, the lung can be compressed from the inside via the Ppm 200 (thereby creating positive airway pressure), and from the outside via the PPC module 300 (thereby creating positive chamber pressure).

The purpose of this bidirectional transpulmonary gradient is to prevent the formation of interstitial edema over long-term isolated lung culture and to treat edema that has already formed (e.g., in previously injured lungs) by pushing the interstitial fluid into the vasculature thus improving lung function (e.g., compliance, diffusion, weight, and size). This gradient can be achieved if the venous pressure can be adjusted relative to the chamber pressure. By adjusting the height of the media reservoir 103, and thereby adjusting the height of the water column in the venous cannula and draining pulmonary venous return to media chamber 103, the venous pressure can be kept at a constant level higher or lower than the chamber pressure. Essentially, the equilibration between the two chambers allows constant pulmonary venous drainage during negative pressure ventilation. In contrast, if equilibration is not maintained and P, is kept constant, a negative pressure in a lung chamber 101 would result in decreased venous drainage or reversal (e.g., partial or complete) in venous flow, while a positive pressure in a lung chamber 101 would collapse pulmonary veins leading to outflow obstruction.

The positive pressure manifold 200 is connected to the tracheal line 112 to enable the bioreactor 100 to generate negative pressure ventilation and generate and maintain positive airway pressure (through the tracheal line 112) throughout inspiration and expiration. The bioreactor 100 is further configured to adapt to a large matrix size (e.g., human adult lungs and human children's lungs) and for long-term culture due to the addition of the equilibration line 118 and the filter occluder 117.

Figure 3:
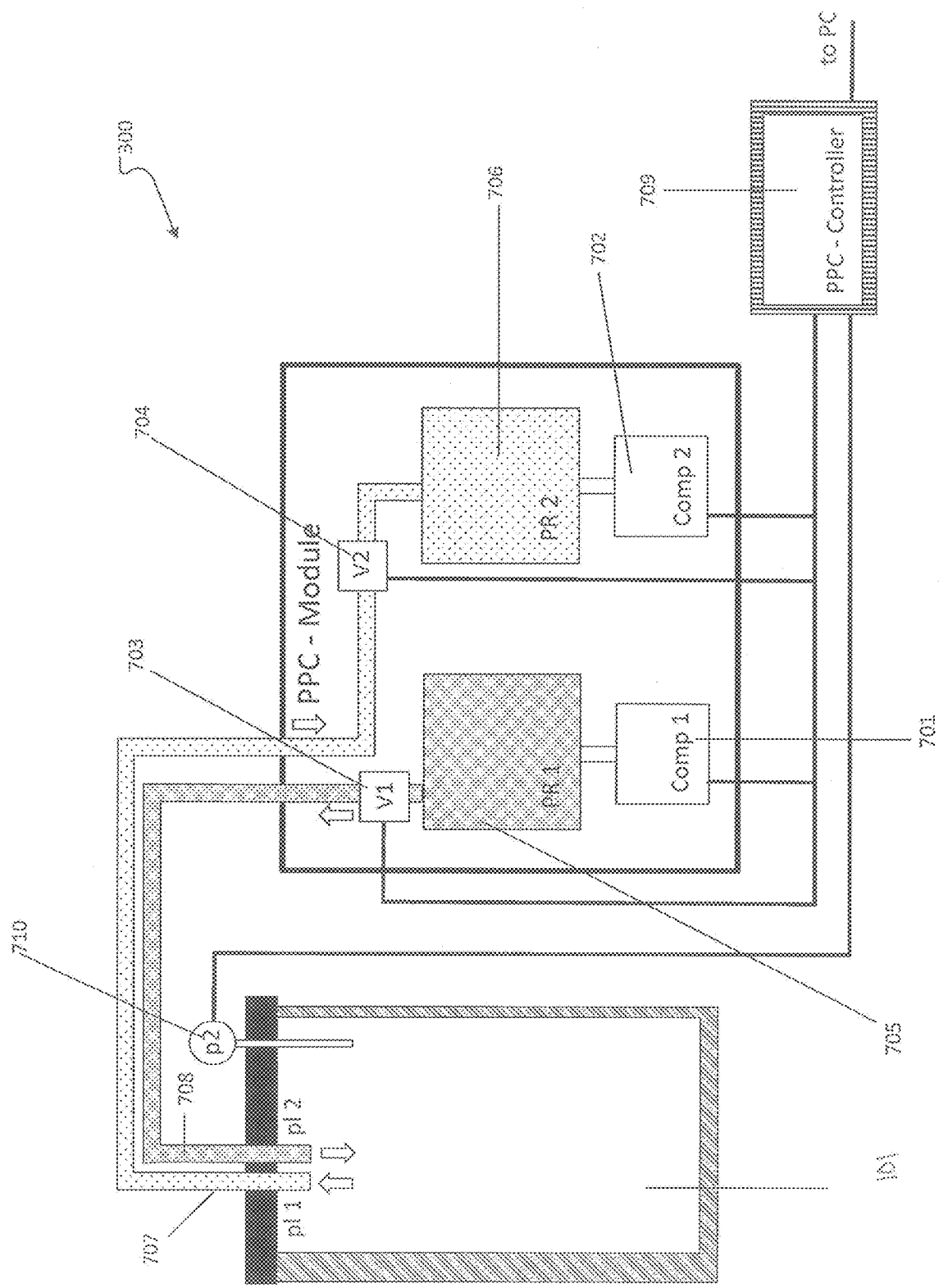
FIG. 3 is a schematic diagram of a pneumatic pressure control module connected to an organ culture chamber.
Figure 4:
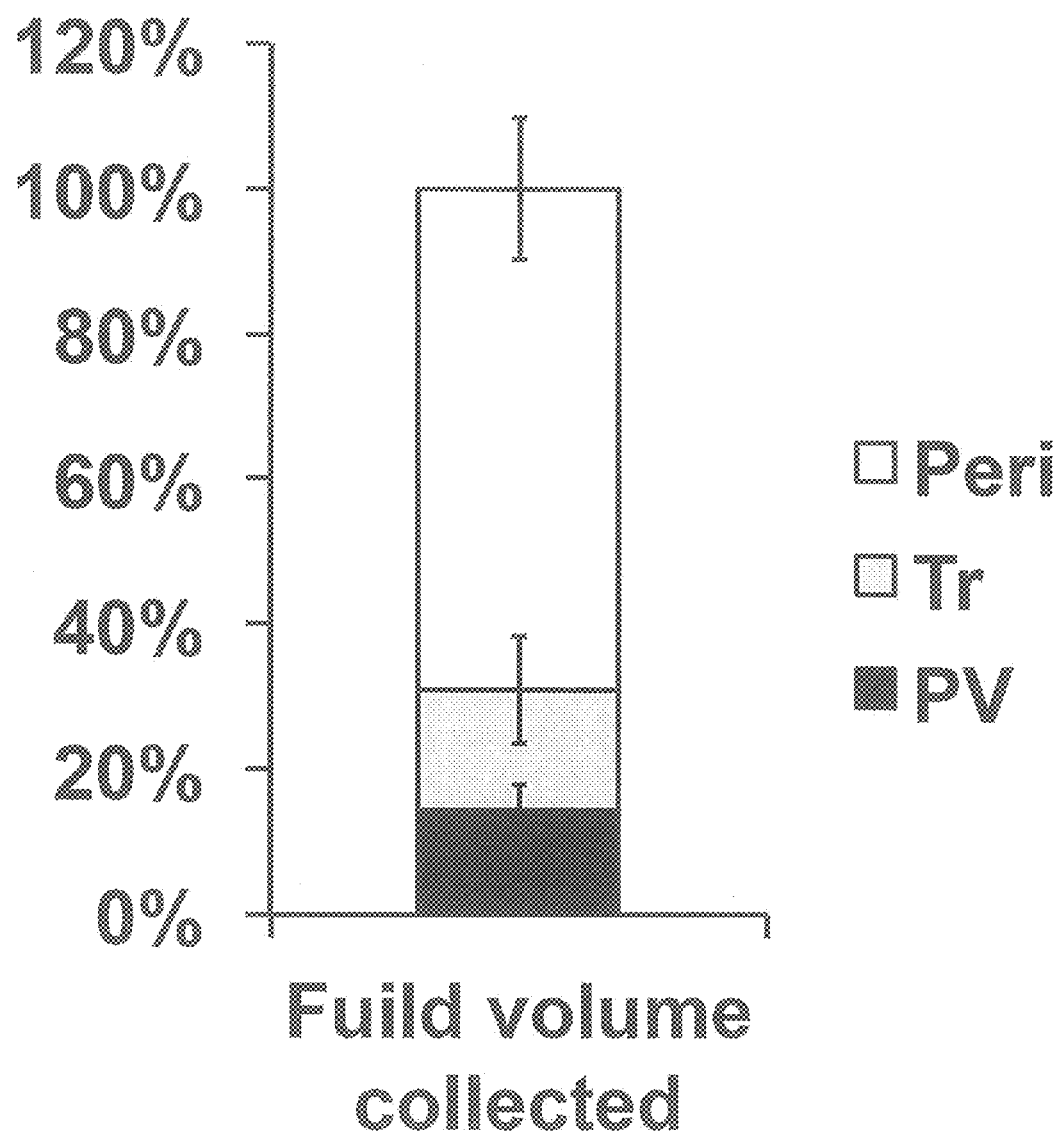
FIG. 4 is a graph showing fluid volumes collected from the pulmonary vein (PV), trachea (Tr) and lung periphery (peri) during microsphere perfusion of acellular rat lungs through the pulmonary artery (PA) (normalized to the total volume collected from the three compartments).

Referring to FIG. 2A, the positive pressure manifold 200 includes a tracheal line portion 304 (e.g., part of tracheal line 112 shown in FIG. 1), a pressure reservoir 302, a pressure release valve 301, a compressor 303 (e.g., a pressured gas source), an inflatable breathing bag 306, and a manifold pressure sensor 308. The tracheal line 304 is connected to the airway of the lung (not shown). The compressor 303 provides positive pressure to the pressure reservoir 302, and the pressure level in the pressure reservoir 302 can be modified by the pressure release valve 301, (e.g., pressure can be reduced). In certain embodiments, the positive pressure manifold 200 is a computerized system that actively regulates pressure in the pressure reservoir 302 in response to the inspiratory and expiratory related pressure variations in the airway (e.g., as recorded by the tracheal pressure sensor 108 or by the manifold pressure sensor 308). The inflatable breathing bag 306 is attached to the pressure reservoir 302 to accommodate sudden volume changes during inspiration and expiration while keeping the pressure in the chamber, trachea, and lung constant. The volume of the inflatable breathing bag 306 may vary depending on the size of the lung being cultured. For example, the volume of the inflatable breathing bag 306 may be between 250 cc and 4000 cc, at least 250 cc, less than 4000 cc, between 300 cc and 3500 cc, between 400 cc and 3000 cc, between 500 cc and 2500 cc, between 600 cc and 2000 cc, between 700 cc and 1500 cc, and between 800 cc and 1000 cc. The material of the inflatable breathing bag 306 can be any flexible, air impermeable and sterilizable material (e.g., latex or rubber). The manifold pressure sensor 308 facilitates both monitoring end-expiratory pressure and enabling flow calculations in the ventilation line.

Figure 2B:
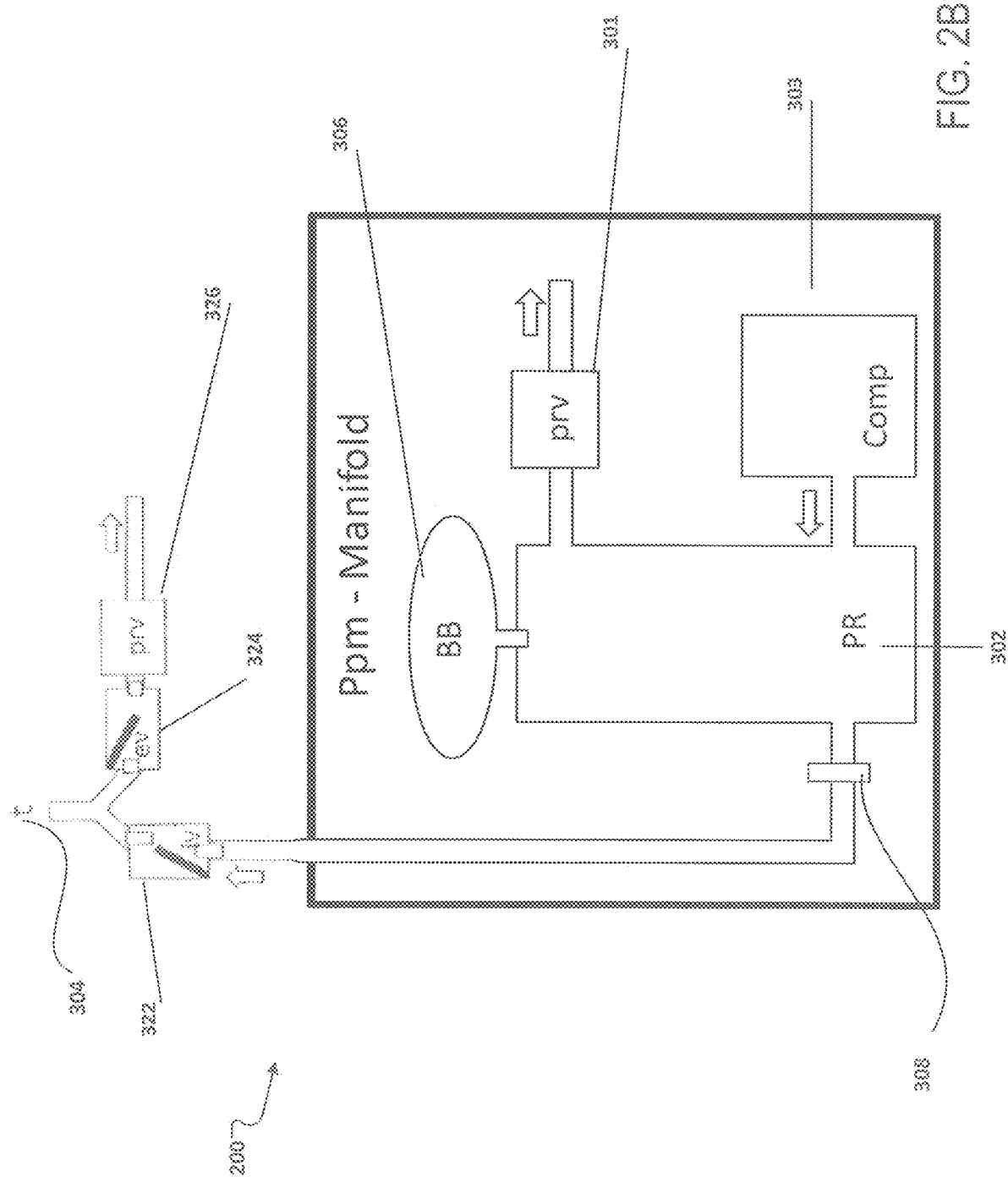

Referring to FIG. 2B, the positive pressure manifold 200 may also include an inspiratory valve 322, and expiratory valve 324 and an expiratory pressure release valve 326. The tracheal line 304 is connected to the airway of the lung (not shown). As described with reference to FIG. 3A, the compressor 303 provides positive pressure to the pressure reservoir 302, and the pressure level in the pressure reservoir 302 can be modified by the pressure release valve 324, (e.g., pressure can be reduced). The tracheal line 304 is also connected to the inspiratory valve 322 and the expiratory valve 324. The inspiratory valve 322 and the expiratory valve 324 are one-way valves that allow fluid, e.g., air, to flow in one direction and that prevent backflow. During the expiratory phase, air flows from the tracheal line 304 through the expiratory valve 324 and the expiratory pressure valve 326 to an exhaust line (not shown). Expired fluid does not enter the pressure reservoir 301 due to the inspiratory valve 322. During the inspiratory phase, air flows from the pressure reservoir through the inspiratory valve 322 to the airway of the lung via the tracheal line 304. The expiratory pressure release valve 324 ensures that the expiratory line retains a positive pressure during an inhalation phase, thus preventing air from flowing through the expiratory line during an inhalation phase.

Referring to FIG. 3, pneumatic pressure control module 300 includes an inlet pressure valve 703, an inlet pressure reservoir 705, an inlet compressor 701, an inlet line 707, an outlet pressure valve 704, an outlet pressure reservoir 706, an outlet compressor 702, an outlet line 708, and a PPC controller 709. The inlet line 707 and the outlet line 708 are connected to the lung chamber 101, which includes a chamber pressure sensor 710. The inlet and outlet compressors 701, 702 charge the inlet and outlet pressure reservoirs 705, 706 with gas (e.g., air). The inlet and outlet pressure valves 703, 704 (e.g., solenoid valves) and inlet and outlet compressors 701, 702 are controlled by the PPC controller 709. During the inspiration phase, outlet valve 704 opens and generates negative pressure in the lung chamber 101. Once the negative target pressure is recorded by the chamber pressure sensor 710 (e.g., −20 cmH$_2$O), the outlet valve 704 closes. Chamber pressures may range from −50 to +100 cmH$_2$O during inspiration and expiration. Once lung compliance approaches that of normal lung, chamber pressure more closely mimics the physiologic range of intrapleural pressure (e.g., −10 to +25 cmH$_2$O). After an appropriate plateau phase, an expiration phase begins in which the inlet pressure valve 703 opens and allows generation of positive pressure inside the lung chamber 101. Once the positive target pressure is recorded by the chamber pressure sensor 710 (e.g., 25 cmH$_2$O), the inlet valve 703 closes. The inlet and outlet pressure reservoirs 705, 706 are sized appropriately to enable quick adjustment of the pressure in the lung chamber 101. The inlet and outlet pressure reservoirs 705, 706 prevent and/or reduce vibration artifacts generated by the inlet or outlet compressors 701, 702. In some embodiments, the slope of the pressure equilibration can be adjusted by an additional resistances valve (not shown) placed in the inlet line 707 and/or outlet line 708. Ventilation can be pressure controlled (PC) or volume controlled (VC).

Other exemplary bioreactors and methods are described, for example in PCT/US2015/020605, filed Mar. 13, 2015 and titled Lung Bioreactor, and U.S. Pat. No. 9,005,885, filed Feb. 24, 2012 and titled Bioartificial Lung, the contents of which are each hereby incorporated by reference in their entirety.

Cell Seeding

In some of the methods described herein, a lung tissue matrix, e.g., decellularized lung tissue matrix or artificial lung matrix, is seeded with cells, e.g., differentiated or regenerative cells.

Any appropriate regenerative cell type, such as naïve or undifferentiated cell types, can be used to seed the lung tissue matrix. The cells may be seeded at a variety of stages including, but not limited to, the stem cell stage (e.g., after induction), progenitor cell stage, hemangioblast stage, or differentiated stage (e.g., CD 31+, vWF+, CD140b+). As used herein, regenerative cells can include, without limitation, progenitor cells, precursor cells, and "adult"-derived stem cells including umbilical cord cells (e.g., human umbilical vein endothelial cells), placenta-derived cells, and fetal stem cells. Regenerative cells also can include differentiated or committed cell types. Stem cells appropriate for the methods and materials provided herein can include human induced pluripotent stem cells (iPSC) and derivatives (e.g., undifferentiated, differentiated endoderm, anteriolized endoderm, TTF-1 positive lung progenitors, endothelial progenitors, and mesodermal progenitor cells, perivascular cells, muscle progenitor cells), human mesenchymal stem cells, human umbilical vein endothelial cells, multipotent adult progenitor cells (MAPC), iPS derived mesenchymal cells, or embryonic stem cells. In some cases, regenerative cells derived from other tissues also can be used. For example, regenerative cells derived from skin, bone, muscle, bone marrow, synovium, placenta, or adipose tissue can be used to develop stem cell-seeded tissue matrices.

In some cases, a lung tissue matrix provided herein can be alternatively or further seeded with differentiated cell types such as (preferably human) epithelial cells and endothelial cells. For example, a lung matrix can be seeded with endothelial cells via the vasculature (e.g. through the arterial line 110, the venous line 111, or both the arterial line 110 and the venous line 111), and seeded with epithelial cells via the airway (e.g., through the tracheal line 112). The lung matrix can also be seeded with one or more cell types (e.g., one or more of types of epithelial and mesenchymal cells, adult peripheral blood-derived endothelial cells, cord blood derived endothelial cells, iPS derived epithelial and endothelial cells, progenitor stage cells (e.g., smooth muscle), adult lung derived cell mixture (e.g., rat human), commercially available small airway epithelial cells or alveolar epithelial cells, Embryonic Stem (ES) cell derived epithelial cells, and/or human umbilical vein endothelial cells (HUVEC).

Delivering vascular-related cells and/or media into acellular lung scaffolds through both the pulmonary artery and pulmonary vein helps to improve cell distribution and distribution. For example, within the lung chamber 101, the cell matrix is perfused antegradely with cells and media to allow seeding of cells to grow on the lung matrix. The perfusion takes place through the arterial line 110 to the pulmonary artery and through the venous line 111 to the pulmonary vein. This configuration permits the cells and media to reach the capillary bed from both the arterial and venous sides and permits the media to diffuse through the acellular basement membrane and exit the matrix via the trachea or across the pleura.

In some cases, a decellularized or artificial lung tissue matrix as provided herein can be seeded with the cell types and cell densities described above by perfusion seeding. For example, a flow perfusion system can be used to seed the decellularized lung tissue matrix within lung chamber 101 via the vascular system preserved in the tissue matrix (e.g., through the arterial line 110). In some cases, automated flow perfusion systems can be used under the appropriate conditions. Such perfusion seeding methods can improve seeding efficiencies and provide more uniform distribution of cells throughout the composition. Quantitative biochemical and image analysis techniques can be used to assess the distribution of seeded cells following either static or perfusion seeding methods. The cells can be introduced into the matrix via the arterial and venous lines (endothelial cells) or through the airway (tracheal) line (epithelial cells). A tissue matrix can be seeded with at least one cell type in vitro at any appropriate cell density. Cell densities for seeding a matrix can be at least $1\times10^3$ cells/gram matrix. Cell densities can range between about $1\times10^5$ to about $1\times10^{10}$ cells/gram matrix (e.g., at least 100,000, 1,000,000, 10,000,000, 100,000,000, 1,000,000,000, or 10,000,000,000 cells/gram matrix) can be used.

In some cases, a decellularized or artificial lung tissue matrix, as provided herein, can be seeded with the cell types and cell densities described above by perfusion seeding. For example, a flow perfusion system can be used to seed the decellularized lung tissue matrix via the vascular system preserved in the tissue matrix (e.g., through the arterial line 110). In some cases, automated flow perfusion systems can be used under the appropriate conditions. Such perfusion seeding methods can improve seeding efficiencies and provide more uniform distribution of cells throughout the composition. Quantitative biochemical and image analysis techniques can be used to assess the distribution of seeded cells following either static or perfusion seeding methods.

In some cases, a tissue matrix can be impregnated with one or more growth factors to stimulate differentiation of the seeded regenerative cells. For example, a tissue matrix can be impregnated with growth factors appropriate for the methods and materials provided herein, for example, vascular endothelial growth factor (VEGF), TGF-β growth factors, bone morphogenetic proteins (e.g., BMP-1, BMP-4), platelet-derived growth factor (PDGF), basic fibroblast growth factor (b-FGF), e.g., FGF-10, insulin-like growth factor (IGF), epidermal growth factor (EGF), or growth differentiation factor-5 (GDF-5). See, e.g., Desai and Cardoso, *Respire. Res.* 3:2 (2002). These growth factors can be encapsulated to control temporal release. Different parts of the scaffold can be enhanced with different growth factors to add spatial control of growth factor stimulation.

Seeded tissue matrices can be incubated for a period of time (e.g., from several hours to about 14 days or more) post-seeding to improve fixation and penetration of the cells in the tissue matrix. The seeded tissue matrix can be maintained under conditions in which at least some of the regenerative cells can multiply and/or differentiate within and on the acellular tissue matrix. Such conditions can include, without limitation, the appropriate temperature (35-38 degree centigrade) and/or pressure (e.g., atmospheric), electrical and/or mechanical activity (e.g., ventilation via positive or negative pressure with positive end expiratory pressure from 1-20 cmH$_2$O, mean airway pressure from 5-50 cmH$_2$O, and peak inspiratory pressure from 5-65cmH$_2$O), the appropriate amounts of fluid, e.g., O$_2$ (1-100% FiO$_2$) and/or CO$_2$ (0-10% FiCO$_2$), an appropriate amount of humidity (10-100%), and sterile or near-sterile conditions. Such conditions can also include wet ventilation, wet to dry ventilation and dry ventilation. In some cases, nutritional supplements (e.g., nutrients and/or a carbon source such as glucose), exogenous hormones, or growth factors can be added to the seeded tissue matrix. Histology and cell staining can be performed to assay for seeded cell propagation. Any appropriate method can be performed to assay for seeded cell differentiation. In general, the methods described herein will be performed in an airway organ bioreactor apparatus, e.g., as described herein.

Thus, the methods described herein can be used to generate a lung that could provide gas exchange to patients either as an extracorporeal device or a transplantable lung tissue graft. As described herein, a transplantable tissue will preferably retain a sufficiently intact vasculature that can be connected to the patient's vascular system.

The bioartificial lung tissues described herein can be combined with packaging material to generate articles of manufacture or kits. There are components and methods for producing articles of manufacture. In addition to the bioartificial tissues, an article of manufacture or kit can further can include, for example, one or more anti-adhesives, sterile water, pharmaceutical carriers, buffers, and/or other reagents for promoting the development of functional lung tissue in vitro and/or following transplantation. In addition, printed instructions describing how the composition contained therein can be used can be included in such articles of manufacture. The components in an article of manufacture or kit can be packaged in a variety of suitable containers.

Vascular Maturation Using a Multi-Phase Culture Program

To facilitate vascular maturation in isolated organ culture, a two-phase culture program can be used to regenerate entire pulmonary vasculature or vasculature portions based on acellular lung scaffolds. For example, in combination with perivascular supporting cells, a two-phase culture program transitioning the regenerated cells from a high to a low angiogenic state can help to promote a vascular maturation process in regenerated lungs that resembles the in vivo lumen formation of typical vascular development.

The cells (e.g., HUVECS, hMSCs, hiPSC-ECs and/or hiPSC-PPC) can be seeded onto the acellular lung scaffold using perfusion seeding (e.g., from both the PA and PV as described elsewhere). Optionally, static culture may follow the perfusion seeding to allow for initial attachment of cells to the vascular basement membrane. Perfusion with media through the PA may continue until the end of culture.

During the first phase, an angiogenic medium, as described elsewhere, is delivered to the seeded lung scaffolds. During the second phase, the seeded lung scaffolds are cultured in a stabilization medium, as described elsewhere. In some examples, the first phase is longer than the second-phase. For example, the first phase can be 6 days while the second phase is only 2 days. An increase of endothelial coverage to reach a plateau, defined by CD31 and VE-cadherin expression, would indicate sufficient vascular remodeling has been achieved, which is the primary goal of the first phase of culture.

The two-phase culture program can be used to recapitulate the organization of the native vasculature unit with endothelial cells forming an interconnected network and with perivascular cells adhering individually around the vascular network. This permits delivery of endothelial cells into acellular a vascular bed as single cell suspension, and these endothelial cells then undergo attachment and remodeling. This leads to an increase in endothelial coverage and the formation of continuous and polarized vascular lumens capable of surrounding and withstanding perfusion fluid flow. These morphological changes during in vitro vascular maturation in regenerated lungs resembles the process of lumen formation during in vivo vascular development.

Cell Seeding—Deriving Clinically Relevant Endothelial and Perivascular Cells

In some of the methods described herein, a lung tissue matrix, e.g., decellularized lung tissue matrix or artificial lung matrix, is seeded with cells, e.g., differentiated or regenerative cells. Efficient endothelial delivery into acellular lung scaffolds and isolated organ culture conditions can contribute to efficient vascular maturation.

The use of patient-derived cells for organ regeneration readily translates to clinical applications because hiPSCs offer the potential to generate all the necessary cell types for organs reconstruction from a single cell source. For example, hiPSC-derived vascular cell types can be used to regenerate the pulmonary vasculature. The hiPSC-derived vascular cell types undergo highly efficient endothelial differentiation with concomitant generation of pericytes to constitute a substantial portion of the total differentiated cells (e.g., at least 50, 60, 70, 80, 90% of the total differentiated cells).

Vascular cell differentiation from human embryonic stem cells and iPSCs can use both a three-dimensional embryoid body and two-dimensional cell culture. For example, hiPSCs can be seeded onto a 2-dimensional surface (e.g., a 6-well plate, or a 6-well plate coated in collagen). While seeded the cells can be treated with inhibitors (e.g., GSK-3 inhibitors such as CHIR99021, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), a 4 Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5 bromoindirubin, 4-Benzyl-2-methyl-1,2,4-thiadiazolidine-3,5-dione (TDZD-8), 2-thio(3-iodobenzyl)-5-(1-pyridyl)[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), a 4 Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), H-KEAPPAPPQSpP-NH2 (L803) and Myr-N-GKEAPPAPPQSpP-NH2 (L803-mts)); in some embodiments the GSK3-beta inhibitor is CHIR99021 (e.g., used at 5-20 uM, e.g., 10-15 uM, e.g., about 12 µM, Stemgent)) and medium (e.g., mTeSR™)) can be used (e.g., for 1 to 24 hr). Expression of the Brachyury gene (a mesodermal progenitor marker) in more than 90% of the cells indicates completion of this phase.

To differentiate the cells, the cells are placed in a complete differentiation medium (e.g., IMDM (Gibco)). The differentiation medium can also include supplemental serum or serum substitutes, compounds, amino acids, media supplements, and/or proteins (e.g., BIT 9500 (STEMCELL Technologies), monothioglycerol (450 mM, Sigma Aldrich), MEM Non-Essential Amino Acids (Gibco), 1% GlutaMAX, 1% P/S, recombinant human BMP4 (PeproTech), VEGF (PeproTech) and bFGF (PeproTech)).

Then, the hiPSC-derived endothelial cells (hiPSC-ECs) and/or hiPSC derived perivascular progenitor cells (hiPSC-PPCs) can be expanded to a scale sufficient for human-sized lung engineering without losing their endothelial identity or proliferation potential. For example, the differentiated cells can be disassociated to single cells (e.g., by using enzymatic cell dissociation reagents such as trypsin or TrypLE (Gibco)), stained with one or more antibodies or isotype controls (e.g., anti-human CD31-BV605, CD140b+, and CD140b-PE antibodies (BD Biosciences)), and separated (e.g., by fluorescence-activated cell sorting (FACS) using FACSAriaII (BD Biosciences)).

After separation, the hiPSC- and hiPSC-PPCs can be cultured in Collagen I (BD Biosciences)-coated flasks, e.g., using EGM-FBS-SB medium, which is EGM-2 without hydrocortisone, supplemented with one or more of 20% defined FBS (Hyclone), 1% Pen/Strep, and a TGFβ receptor I (ALK5) inhibitor, e.g., SB431542, SB525334, SD-208, EW-7197, SB505124, or Galunisertib (LY2157299); in some embodiments the inhibitor is SB431542 (e.g., at 5-20 μM, e.g., 8-15 μM, e.g., 10 μM).

For differentiation towards smooth muscle cell-like phenotype, hiPSC-PPCs were cultured in Smooth Muscle Growth Medium-2 (SmGm2, Lonza) until upregulation of a-SMA and Calponin protein in more than 90% of the cells, (e.g., for 6 days).

In Vitro and In Vivo Characterization of Vascular Functions

Any appropriate method(s) can be performed to assay for lung function before or after transplantation. For example, methods can be performed to assess tissue healing, to assess functionality, and to assess cellular in-growth. In some cases, tissue portions can be collected and treated with a fixative such as, for example, neutral buffered formalin. Such tissue portions can be dehydrated, embedded in paraffin, and sectioned with a microtome for histological analysis. Sections can be stained with hematoxylin and eosin (H&E) and then mounted on glass slides for microscopic evaluation of morphology and cellularity. For example, histology and cell staining can be performed to detect seeded cell propagation. Assays can include functional evaluation of the transplanted tissue matrix or imaging techniques (e.g., computed tomography (CT), ultrasound, or magnetic resonance imaging (e.g., contrast-enhanced MRI)). Assays can further include functional tests under rest and physiologic stress (e.g., body plethysmography, lung function testing). Functionality of the matrix seeded with cells can be assayed using various methods, for example, histology, electron microscopy, and mechanical testing (e.g., of volume and compliance). Gas exchange can be measured as another functionality assay. To assay for cell proliferation, thymidine kinase activity can be measured by, for example, detecting thymidine incorporation. In some cases, blood tests can be performed to evaluate the function of the lungs based on levels of oxygen in the blood. Alternatively or in addition, ex vivo perfusion using fluorescently labeled dextran solutions can be performed to quantify the intravascular dextran retention, which indicated vascular integrity and perfusability. Fresh isolated cadaveric rat lungs have an intravascular dextran retention of 100%. Cadaveric lungs after 6-hour cold-ischemia, which is a clinically relevant low-grade injury model compatible with transplantation, typically have intravascular detran retentions of about 87.0%±5.4% (e.g., a range of 80.6% to 92.9%).

To facilitate functionality assays during culture, any line of the bioreactor apparatus described herein may include sampling ports to allow for single or real time measurements of functionality parameters (e.g., pH, glucose, lactate, Na, K, Ca, Cl, Bicarb, $O_2$, $CO_2$, sat). Metabolites may also be used to monitor cell number and viability using colorimetric assays, and biochemical assays may be used to monitor cell maturation (e.g., measuring surfactant protein etc.). For example, an increased concentration of surfactant can indicate that the culture lung possesses sufficient epithelial cells to withstand dry ventilation. In some cases, endothelial barrier function may be used as a marker of vascular maturity. Lungs can be perfused with different sizes of molecules (such as dextrans of defined sizes and albumin), microbeads or microspheres (increasing sizes from 0.2 to 5 um), as well as isolated red blood cells. Bronchoalveolar lavage fluid can then be sampled to assess leakage of these markers into the alveolar space. For example, 500-kDa dextran can be used in combination with a Bronchoalveolar lavage assay to determine the percentage of dextran retained within the vascular compartment. An increase in the percentage of dextran retained indicates an improvement in the barrier function because barrier function to dextran is dependent on viable and functional endothelium, while dextran will diffuse across a denuded vascular basement membrane (e.g., in an acellular lung) over time during constant perfusion. For example, a cadaveric lung may retain substantially all of the dextran within the vascular compartment, while acellular lungs may retain a small percentage of the dextran (e.g., 10.0%±8.0%, e.g., from 3-20%, e.g., 3.1% to 18.7%). Leakage of these markers into the alveolar space greater than a tolerated minimum (for example >10% of 4 um microbeads (e.g., 10% to 100% or 20% to 100% would indicate the lung is not sufficient to withstand dry ventilation), or greater than 20% of 0.2 um microbeads (20% to 100%, or 30% to 100% would indicate the lung is not sufficient to withstand dry ventilation) indicates that the lung is not sufficiently mature to withstand dry ventilation.

In some cases, molecular biology techniques such as RT-PCR can be used to quantify the expression of metabolic (e.g. surfactant protein, mucin-1) and differentiation markers (e.g. TTF-1, p63, surfactant protein C). Any appropriate RT-PCR protocol can be used. Briefly, total RNA can be collected by homogenizing a biological sample (e.g., tendon sample), performing a chloroform extraction, and extracting total RNA using a spin column (e.g., RNeasy® Mini spin column (QIAGEN, Valencia, Calif.)) or other nucleic acid-binding substrate. In other cases, markers associated with lung cells types and different stages of differentiation for such cell types can be detected using antibodies and standard immunoassays.

EXAMPLES

The following specific examples further illustrate the invention.

Example 1

Study of Acellular Pulmonary Vascular Bed

The purpose of this example is to identify the perfusion properties of an acellular vascular bed in a whole lung scaffold using an in vitro microsphere perfusion assay. By quantifying microspheres collected from PV, trachea and lung periphery, we demonstrated both continuity and integrity of vascular basement membrane after decellularization, and thereby confirmed the possibility of compartment-specific cell delivery in acellular lung scaffolds. Microsphere quantification further implied that fluid-driven hydrostatic pressure loss but not particle leakage was the main reason for the low passing-through efficiency. By applying these findings to recellularization, efficient and homogeneous endothelial coverage is achieved by the combined arterial and venous cell delivery.

Methods

Cadaveric lungs were explanted from male Sprague-Dawley rats (250-300 g, Charles River Laboratories) after systemic heparinization. The pulmonary artery (PA) was cannulated with an 18G cannula (McMaster-Carr), the pulmonary veins (PV) was cannulated through the left atrium appendage (LAA) using a miniball cannula with tip basket (1.9 mm ID) (Harvard Apparatus), and the aorta was ligated. Decellularization was done by perfusing the PA (constant pressure, 40 mmHg) sequentially with heparinized (10 units/ml) phosphate-buffered saline (PBS, 10 min), 0.1% sodium dodecyl sulfate in deionized water (2 hours), deionized water (15 minutes) and 1% Triton X-100 in deionized water (10 minutes). Resulting scaffolds were washed with PBS containing antibiotics and antimytotics for 72 hours to remove residual detergent and cellular debris. All reagents are from Sigma Aldrich.

For whole-mount imaging of decellularized rat lungs after microsphere perfusion from the PA, decellularized lungs were perfused through the PA under 20 mmHg with 30 ml of PBS containing 1:100 diluted green FluoSpheres (0.2 µm, 505/515, Invitrogen). For whole-mount imaging of decellularized lungs after microsphere perfusion from both the PA and PV, decellularized lungs were perfused through the PA with 30 ml of PBS containing 1:100 diluted green FluoSpheres (0.2 µm, 505/515) with the PV cannula open, and then perfused through the PV with 30 ml of PBS containing 1:100 diluted red FluoSpheres (0.2 µm, 580/605) with the PA cannula open. Individual lobes were dissected from decellularized lungs after microsphere perfusion, and imaged using a Nikon Eclipse TE200 microscope at 4× magnification.

For quantification of microsphere perfusion and leakage in decellularized rat lungs, the trachea was also cannulated with an 18G cannula (McMaster-Carr). Decellularized lungs were perfused through the PA under 40 mmHg with 30 ml of PBS containing a mixture of 1:10 diluted green FluoSpheres (0.2 µm, 505/515) and red FluoSpheres (0.02 µm, 580/605). During perfusion, fluids drained from PV cannula and lung periphery were collected. Trachea cannula was closed during perfusion, and fluid accumulated in the airway was collected after perfusion by releasing the trachea cannula. The volumes of fluids collected from all the three compartment (PV, trachea and periphery) were measured, and their fluorescence intensities were measured using SpectraMax Microplate Reader at 485 nm (ex)/538 nm (em) for 0.2-µm green FluoSpheres and at 544 nm (ex)/590 nm (em) for 0.02-µm red FluoSpheres.

Figure 5A:
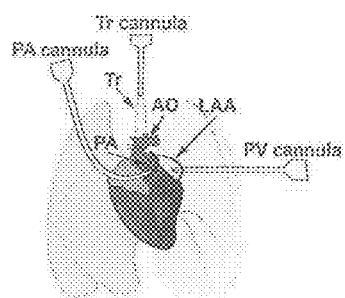
FIG. 5A is an image showing the pulmonary artery (PA) and trachea (Tr) directly cannulated, the PV cannulated through the left atrial appendage (LAA), and the aorta (AO) ligated. This cannulation strategy allowed perfusion though both the PA and PV, and fluid collection from the trachea (Tr) and PV.

Results:

To examine properties of the acellular pulmonary vascular bed in the resulting whole lung scaffolds, the PV via the left atrial appendage, the trachea, and the PA were cannulated (FIG. 5A). As expected, decellularization led to a near complete loss of barrier function, and free filtration of a crystalloid solution such as phosphate buffered saline (PBS) across the vascular basement membrane from PA and PV to interstitial space, across the pleura, and into alveolar spaces and airways. The majority of PBS infused into the PA drained from the lung periphery and the trachea, while only 12.4%±0.7% of volume could be collected from the PV (FIG. 11). This is in line with the observation that during decellularization, detergent perfused through the PA permeabilized the lung vasculature and efficiently lysed cellular components in the entire lung parenchyma.

Figure 5B:
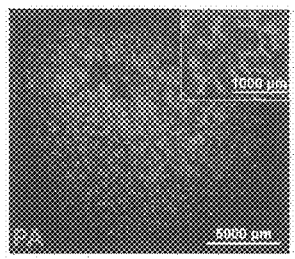
FIG. 5B is an image showing representative whole-mount image of an acellular rat lung perfused with green-fluorescent microspheres (0.2 µm) through the PA.
Figure 5C:
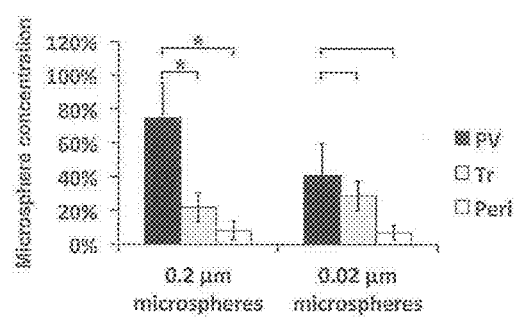
FIG. 5C is a graph showing the concentration of 0.2-µm and 0.02-µm microspheres in the fluids collected from the PV, trachea (Tr) and lung periphery (peri) during their perfusion through the pulmonary artery (PA), normalized to microsphere concentrations of the input.
Figure 5D:
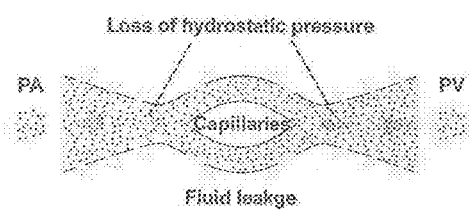
FIG. 5D is a diagram showing microsphere perfusion through the PA and PV of acellular lungs, highlighting fluid leakage along the vascular tracks and gradual reduction of hydrostatic pressure during perfusion.

To examine the continuity and integrity of the vascular basement membrane, and to model perfusion with solutions containing corpuscular elements, acellular whole lungs were perfused with PBS containing fluorescent microspheres (0.2 µm). Neither obvious leakage of microspheres into airways or across the pleura during perfusion under physiologic pressure through the PA (at 20 mmHg), nor obvious microsphere drainage from the PV were observed. Using lung whole mounts, the intrapulmonary entrapment of perfused microspheres (FIG. 5B) was confirmed. When the perfusion pressure through the PA increased from 20 mmHg to 40 mmHg, microspheres could be collected from the PV at a concentration close to input (74.6%±20.8%) and significantly higher than that in fluids collected from the trachea (Tr, 22.7%±12.2%, $p<0.05$) and lung periphery (Peri, 5.7%±5.1%, $p<0.05$) (FIG. 5C). This finding confirmed preserved integrity and continuity of pulmonary vascular basement membrane after decellularization. However, the total amount of microspheres collected from the PV was only 10.3%±0.9% of the total amount infused. This indicated that microspheres, when perfused from the arterial side did not pass through the capillary bed efficiently. This inefficiency can be related to the rapid loss of hydrostatic pressure within the vascular bed, as the aqueous phase diffuses through the very permeable basement membrane, and intravascular microsphere concentration in the remaining solution increases (FIG. 5D).

Figure 5E:
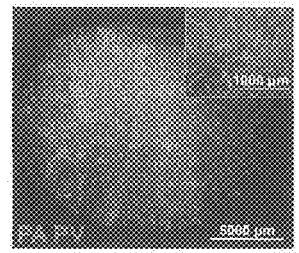
FIG. 5E is a representative whole-mount image of an acellular rat lung perfused with green-fluorescent microspheres (0.2 µm) through the PA and red-fluorescent microspheres (0.2 µm) through the PV.

By sequentially perfusing microspheres labeled with different colors via the PA and PV, it is clear that neither arterial nor venous microspheres leaked into alveolar space or airways. Instead, microsphere opacified vascular channels were generally mutually exclusive (FIG. 5E). This indicates that efficient vascular cell delivery would benefit from perfusion from both arterial and venous side to reach the entire pulmonary vascular bed.

Conclusion:

Found that micrometer-diameter particles do not efficiently pass through the acellular pulmonary capillary bed under physiological pressure.

Example 2

Improvement of Endothelial Delivery

The purpose of this example is to demonstrate the re-establishment of a viable endothelium on acellular rat lung scaffolds and to confirm the integrity of the vascular basement membrane after decellularization.

Methods

Cell seeding into decellularized rat lungs was performed in bioreactors, similar to those described herein, allowing cell delivery and perfusion from both the PA and PV. The trachea was cannulated and open to the inside of bioreactor through a port that was about 5 cm above the level of the PA. Decellularized lung scaffolds were primed by perfusion at 1 ml/min with 100 ml of Hank's balanced salt solution with human Fibronectin (2.5 µg/ml) for 1 hour, washed with Hank's balanced salt solution for 1 hour, and equilibrated in respective culture medium for at least 1 hour before cell seeding. For endothelial delivery through the PA, 40 million HUVECs were resuspended in a single seeding chamber with 100 ml EGM-2, and seeded through the PA under 30-mmHg gravity (n=3). For endothelial delivery through the PA and PV, 40 million HUVECs were resuspended in two separate seeding chambers (each with 20 million HUVECs in 100 ml EGM-2), and seeded simultaneously through the PA and PV under 30-mmHg gravity (n=3). 2 hours static cultured were performed allowing cell attachment, and then perfusion was initiated at 1 ml/min from both the PA and PV. Reseeded lungs were harvested for histological analysis after 1 day of culture.

Fluorescence images of CD31 and laminin were taken separately from the same field using Nikon Eclipse TE200 microscope. Images were converted to binary images, skeletonized and dilated using ImageJ (NIH). Pixel numbers of processed images were counted using ImageJ, which indicated the coverage of either endothelial cells (CD31) or lung matrix (laminin) in the entire field. Endothelial coverage of regenerated lungs was defined as CD31 coverage normalized to laminin coverage. For each regenerated lungs, pictures were taken from 5 representative fields at 4× magnification. Endothelial coverage of each lung was presented as the averaged coverage of that from the 5 fields. Endothelial coverage was quantified on acellular rat lungs seeded with HUVECs from the PA and after 1 day of culture (n=3), on acellular rat lungs seeded with HUVECs from PA&PV and after 1 day of culture (n=3).

Results:

To re-establish viable endothelium on acellular rat lung scaffolds, fluorescently labeled human umbilical vein endothelial cells (HUVECs) were seeded via perfusion through the PA. This resulted in a similar distribution pattern of engrafted cells as previously observed with microsphere perfusion (FIG. 6 and FIG. 5B). This was also confirmed by the histological assessment showing patchy endothelial distribution at 1 day after HUVEC delivery from the PA alone (FIG. 5F).

To improve cell engraftment and distribution, deliver endothelial cells were delivered into acellular lung scaffolds by perfusion through both the PA and PV. To quantitatively assess endothelial coverage of reseeded acellular rat lungs, the extent of overlap between the immunostaining for the abundant lung extracellular matrix protein Laminin and the area of re-endothelialization labeled by CD31 staining (FIG. 5F-I) is measured.

Figure 5F:
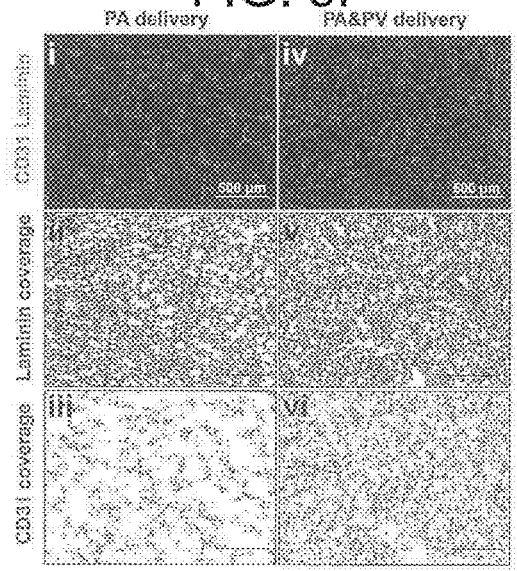
FIG. 5F is a representative image of endothelial coverage of regenerated lungs at 1 day after human umbilical vein endothelial cell (HUVEC) delivery through the PA (i,ii,iii) or through the PA&PV (vi,v,vi). The upper panel showed fluorescent images of CD31 (red, endothelial cells) and Laminin (green, lung matrix) (i,vi). The middle panel showed processed image of Laminin (from that of upper panel) for its coverage quantification (ii,v). Lower panel showed processed image of CD31 (from that of upper panel) for its coverage quantification (iii,vi).
Figure 5G:
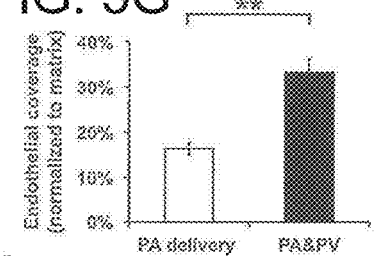
FIG. 5G is a graph showing quantification of CD31 (endothelial) coverage normalized to Laminin (matrix) coverage at 1 day after cell delivery.
Figure 5H:
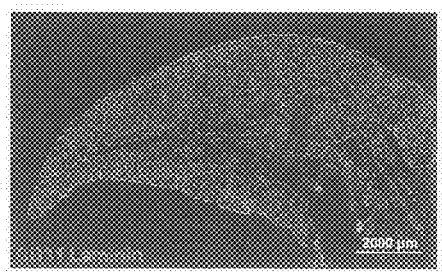
FIG. 5H is a representative stitched image showing endothelial coverage of an acellular rat lung lobe at 1 day after HUVEC delivery through the PA&PV (CD31, red; Laminin, green).
Figure 6:
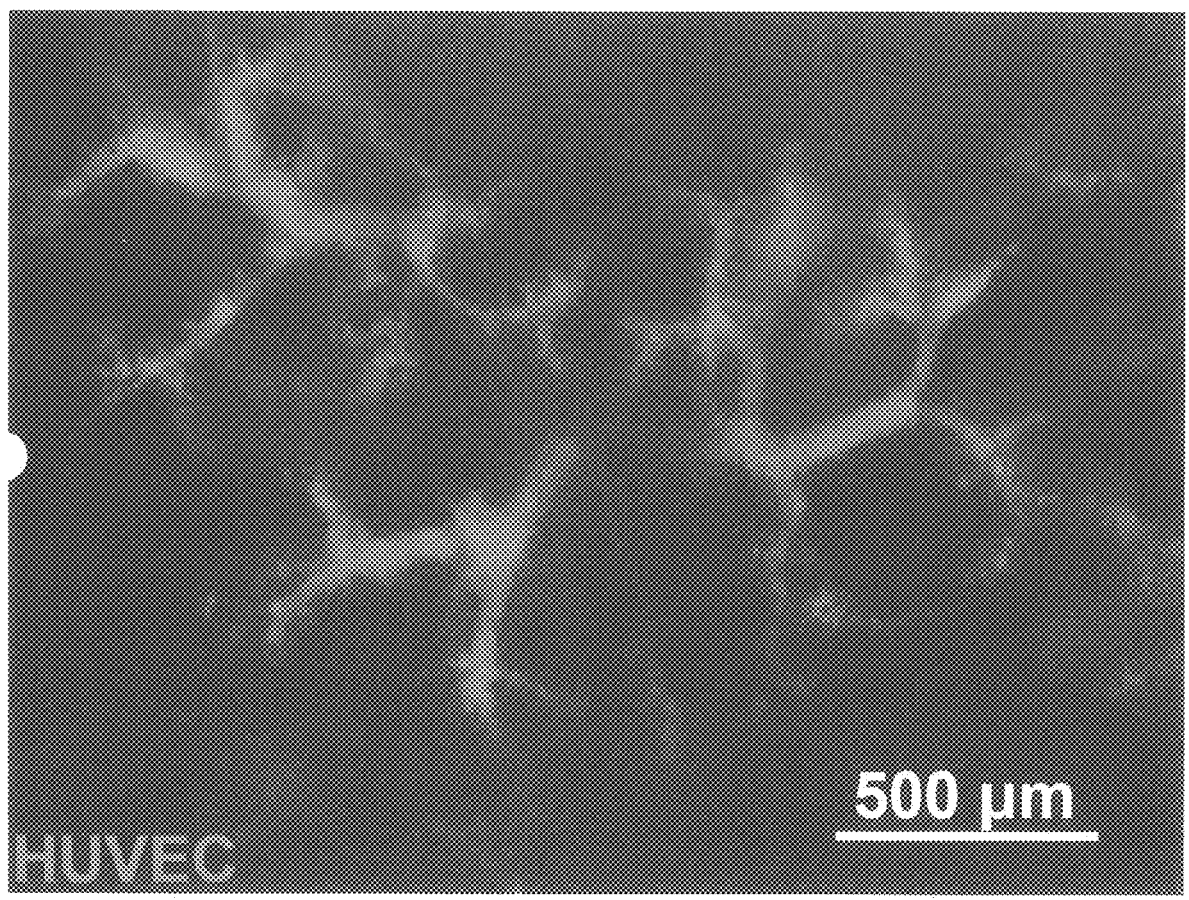
FIG. 6 is a whole-mount image of an acellular rat lung seeded with fluorescently labeled HUVECs.
Figure 8:
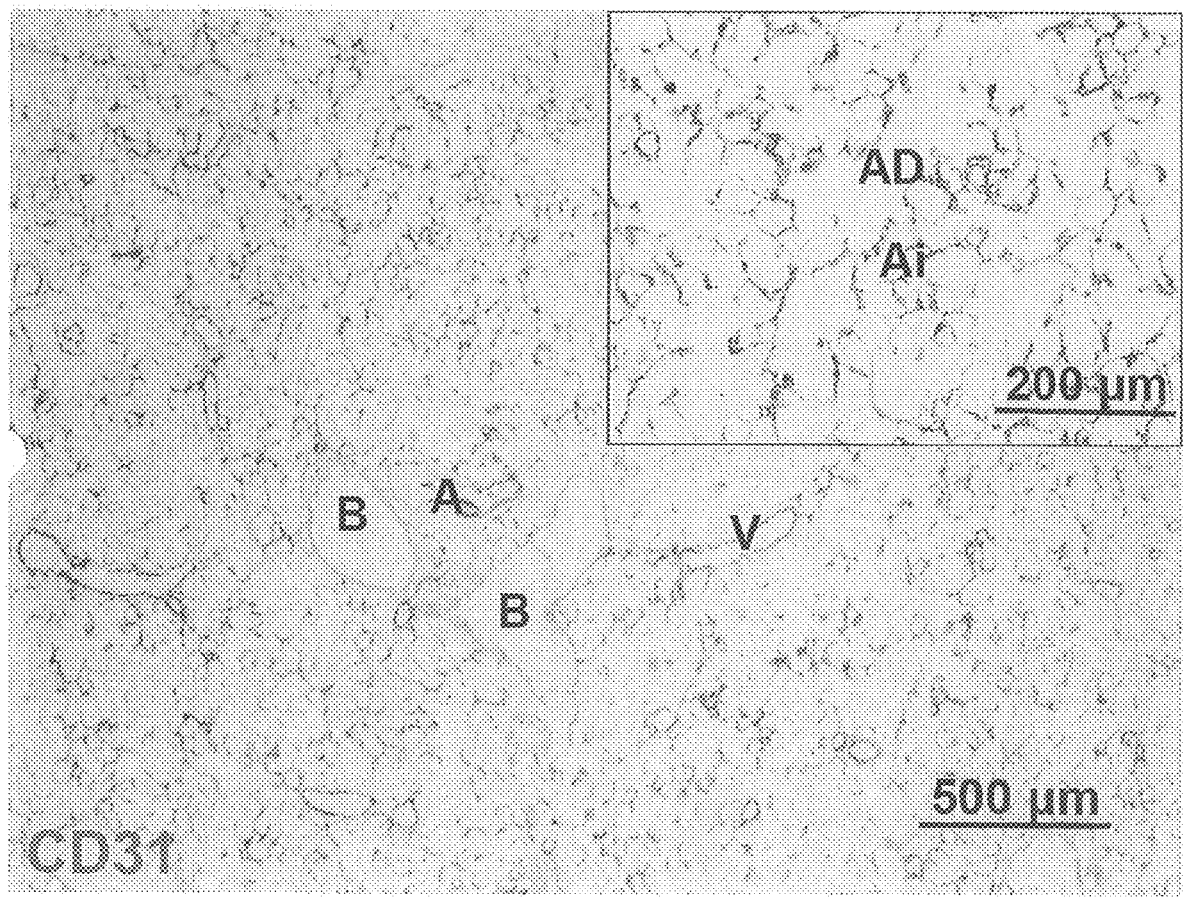
FIG. 8 is an image showing vascular compartment-specific delivery of endothelial cells. A representative image of CD31 immunohistochemical staining of an acellular rat lung at 1 day after HUVEC delivery through the PA&PV (CD31, brown) demonstrating well re-endothelialization of arteries (A) and veins (V), and absence of endothelial cells in bronchus (B). Ai, alveoli; AD, alveolar duct.

Combined arterial and venous delivery led to greater coverage and a more homogenous distribution of endothelial cells (FIG. 5F-iv, H). Quantification of the resulting endothelial coverage at 1 day after seeding indicated that the endothelial coverage obtained from combined arterial and venous delivery was significantly higher than that produced by arterial delivery alone (33.2%±2.9% versus 16.3%±1.4%, $p<0.01$) (FIG. 5G). As observed under microsphere perfusion, combined arterial and venous endothelial delivery under constant pressure was highly specific to the vascular compartment with absence of endothelial cells in the main airway branches (FIG. 8), thereby confirming the integrity of vascular basement membrane after decellularization.

Example 3

Vascular Maturation During In Vitro Culture

The purpose of this example is to demonstrate efficient and active vascular remodeling, which closely mimics vascular development in vivo, in a complex three-dimensional scaffold (e.g., an acellular lung scaffold). After cell delivery and retention, the transition from an acellular vascular bed filled with endothelial cells to perfusable vascular lumen relies on an active vascular remodeling that closely mimics vascular development in vivo.

Methods

For long-term in vitro culture of acellular rat lungs regenerated with HUVECs about 40 million HUVECs were seeded into acellular lung scaffolds from both the PA and PV as described above, and cultured in EGM-2 for 14 days (n=3) with perfusion from both the PA and PV at 1 ml/min from each side. Medium was changed every other day.

For two-phase culture of acellular rat lungs regenerated with HUVECs and hMSCs (referred to as HUVEC-hMSC lungs), 40 million HUVECs were mixed with 20 million hMSCs and seeded into acellular lung scaffolds from both the PA and PV as described above. After 2 hours static culture, perfusion was re-initiated at 1 ml/min from both the PA and PV. Starting from day 1, PV cannula was released, and perfusion was switched to 4 ml/min from the PA only, which remained until the end of culture. HUVEC-hMSC regenerated lungs were cultured for totally 8 days with the initial 6 days in angiogenic medium and subsequent 2 days in stabilization medium.

Angiogenic medium was Medium 199 (Gibco) supplemented with 10% FBS, 1% Insulin-Transferrin-Selenium (Gibco), ascorbic acid (50 mg/ml, STEMCELL Technologies), recombinant human VEGF (40 ng/ml), bFGF (40 ng/ml) and 1% P/S.

Stabilization medium was Medium 199 supplemented with 2% FBS, 1% Insulin-Transferrin-Selenium, ascorbic acid (50 mg/ml), recombinant human VEGF (20 ng/ml), bFGF (20 ng/ml), forskolin (10 µM, Cayman Chemical), hydrocortisone (110 nM, Sigma Aldrich) and 1% P/S. HUVEC-hMSC regenerated lungs were harvested for functional and histological assessment on day 8.

Figure 7A:
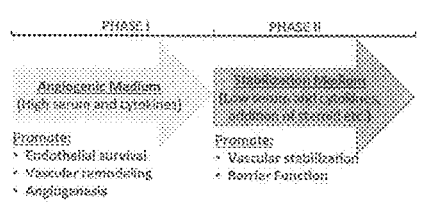
FIG. 7A is a diagram showing the two-phase culture strategy.

Results:

During phase I, the lung was exposed to high levels of serum and angiogenic growth factors (referred to as angiogenic medium) to promote endothelial survival, migration and vascular remodeling. However, pro-angiogenic factors can lead to increased endothelial permeability and decreased barrier function. To offset this tendency, phase 2 of culture stabilized the pre-formed vasculature and strengthen barrier function using a stabilization medium containing lower levels of serum and angiogenic growth factors (e.g., Forskolin and hydrocortisone) that reduce endothelial permeability and improve barrier function (FIG. 7A). Angiogenic medium was Medium 199 (Gibco) supplemented with 10% FBS, 1% Insulin-Transferrin-Selenium (Gibco), ascorbic acid (50 mg/ml, STEMCELL Technologies), recombinant human VEGF (40 ng/ml), bFGF (40 ng/ml) and 1% P/S. Stabilization medium was Medium 199 supplemented with 2% FBS, 1% Insulin-Transferrin-Selenium, ascorbic acid (50 mg/ml), recombinant human VEGF (20 ng/ml), bFGF (20 ng/ml), forskolin (10 µM, Cayman Chemical), hydrocortisone (110 nM, Sigma Aldrich) and 1% P/S.

Figure 7B:
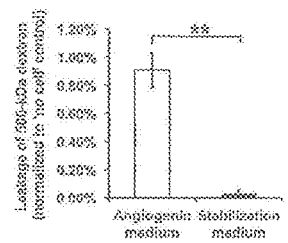
FIG. 7B is a graph showing relative leakage of 500-kDa dextran in HUVEC transwell permeability assays when cultured in Angiogenic or Stabilization Medium for 2 days. Leakage values were normalized to those of transwells without HUVECs ('no cell' control).

To test the effect of media on barrier function after a short exposure to, for example, angiogenic inducers or inhibitors, a dextran transwell permeability assay as used. To evaluate the media's function on endothelial permeability during long-term in vitro culture of regenerated lungs, the dextran transwell permeability assay was modified by exposing HUVEC monolayers to angiogenic medium and stabilization medium for 2 days to study their chronic effects. HUVEC monolayers cultured in stabilization medium displayed significantly improved barrier function compared to those cultured in angiogenic medium (FIG. 7B).

Figure 7C:
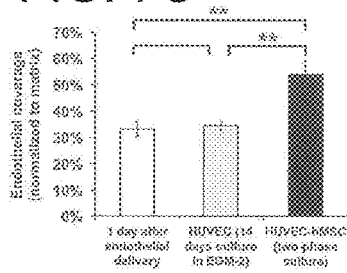
FIG. 7C is a graph showing a quantification of endothelial coverage of HUVEC regenerated lungs after 14-day culture in EGM-2 and human umbilical vein endothelial cell-human mesenchymal stem cells (HUVEC-hMSC) regenerated lungs after two-phase culture (8 days), compared to the coverage of HUVEC regenerated lungs at 1 day after cell delivery. Coverage was quantified by normalizing the coverage of CD31 to that of Laminin.

To regenerate lung vasculature based on acellular rat lung scaffolds, HUVECs and perivascular supporting hMSCs were co-seeded and cultured the regenerated lungs (referred to as HUVEC-hMSC lungs) for 6 days in angiogenic medium and then for 2 days in stabilization medium. To assess the efficacy of this co-seeding and culture strategy on vascular remodeling and regeneration, the endothelial coverage was quantified. A significant increase in endothelial coverage of HUVEC-hMSC lungs at the end of two-phase culture compared to that at 1 day after endothelial delivery (54.0%±5.0% versus 33.2%±2.9%, p<0.01) (FIG. 7C). Large field stitched image further confirmed the homogeneity of endothelial coverage throughout the lung (FIG. 7D). In comparison, acellular rat lung scaffolds were seeded with HUVECs only without perivascular cells and the regenerated lungs (referred to as HUVEC lungs) were cultured for 14 day in conventional EGM-2 medium. Although endothelial cells remained viable in the HUVEC lungs over the entire culture period, the endothelial coverage at the end of conventional culture was only slightly increased compared to that at 1 day after seeding (34.5%±1.6% versus 33.2%±2.9%, p=0.55), and significantly lower than that in HUVEC-hMSC lungs after two-phase culture (34.5%±1.6% versus 54.0%±5.0%, p<0.01). This demonstrates the benefit of including perivascular supporting cells and growth factor stimulation in promoting vascular remodeling in regenerated lung culture (FIG. 7C).

In HUVEC-hMSC regenerated lungs at the end of two-phase culture, while endothelial cells were interconnected forming a network, hMSCs appeared as individual cells adhering to the vascular network (FIG. 7E-I). This closely mimicked the endothelial-pericyte organization in native lungs. The establishment of apical-basal polarity is one of the major morphological milestones for vascular lumen formation. Specific localization of Podocalyxin-like (PODXL) on the vascular luminal surface and Collagen IV (COLIV) on the basement surface can be observed in HUVEC-hMSC regenerated lungs at the end of culture (FIG. 7E-ii). This confirmed lumen formation at both macrovascular and capillary levels. To assess barrier properties, tight junctions were examined by ZO-1 staining, and observed enrichment of ZO-1 proteins at the endothelial borders by the end of two-phase culture (FIG. 7E-iii).

Example 4

In Vitro and In Vivo Assessment of Vascular Function

The purpose of this example is demonstrate a non-invasive method to assess vascular functions of regenerated lungs during isolated organ culture.

Methods

The lung under testing were placed on top of a 150-cm petri dish in the prone position with the PA connected to perfusion line, and with the PV cannula open to the level of the lung, and with the trachea cannula open to the level about 5 cm above that of the PA. 25 ml of PBS or medium containing 500-kDa dextran (0.2 mg/ml) was perfused into the lung under a gravity equals to 20 mmHg. During perfusion, fluids drained from the PV cannula and lung periphery were collected, as PV fluid and periphery fluid, respectively. After perfusion, the trachea cannula was lowered allowing fluid accumulated in the airway to drain into a separate petri dish, as trachea fluid. 5 ml of blank perfusate was then administered into the trachea cannula using a syringe. The fluid passively drained from the trachea cannula after removal of the syringe was collected as BAL fluid. The total amount of dextran in the PV, periphery, trachea and BAL fluids was quantified by measuring the fluorescence intensity and volume.

The dextran concentration was calculated from the fluorescence intensity based on a standard curve. Dextran in the PV fluid was referred to as intravascular dextran, while dextran in the periphery, trachea and BAL fluids was referred to as extravascular dextran. Dextran perfusion and BAL assay was performed on freshly isolated cadaveric rat lungs (n=3), on acellular rat lungs (n=3), and on cadaveric rat lungs after exposure to 6-hour cold ischemia (n=4). 6-hour cold ischemia was produced by incubating freshly isolated rat lungs in ice-cold PBS for 6 hours at 4° C. Dextran perfusion and BAL assay was also performed on HUVEC-hMSC regenerated rat lungs on day 3, 6 and 8 of culture (n=3), and was performed on hiPSC regenerated rat lungs on day 2, 4 and 6 of culture (n=3).

PA pressure in HUVEC-hMSC (n=3) and hiPSC (n=3) regenerated rat lungs was measured daily using a Pressure-MAT Single-Use Sensor (PendoTECH) and recorded using HART-Regen software (Harvard Apparatus). Before each measurement, PA perfusion was paused for 5 to 10 min allowing the pressure to return to and stabilize at the baseline and the baseline pressure was recorded for 5 min. Then, PA perfusion was re-initiated at 4 ml/min, and PA pressure was recorded for 2 hours. At the end of each measurement, PA perfusion was paused again for 5 min to ensure there is no significant drift of the pressure baseline before and after the recording. PA pressure was calculated by subtracting the averaged pressure during perfusion by that of the baseline.

For measuring wet/dry ratio, the accessary lobe of each lung was dissected out, and placed on a dry plastic surface for 30 seconds allowing fluid to drain from major vessels, and then the wet weight was measured. The dry weight of the same accessary lobe was measured after being lyophilized overnight. The wet/dry ratio was calculated by dividing the wet weight by the dry weight. Measurement of Wet/dry ratio was performed on cadaveric rat lungs (n=3), on acellular rat lungs (n=3) and on cadaveric rat lungs after exposure to 6-hour cold ischemia (n=4) right after the dextran perfusion and BAL assay. Measurement of Wet/dry ratio was performed on HUVEC-hMSC (n=3) and hiPSC (n=3) regenerated lungs at the end of culture.

Orthotopic transplantation of regenerated rat lungs were performed on Sprague-Dawley rats (350-400 g) with immunosuppression. Immunosuppression was achieved by subcutaneously injection of cyclosporine A (Sigma-Aldrich) prepared in 90% olive oil (Sigma-Aldrich) and 10% ethanol (Sigma-Aldrich) at 10 mg/kg/day daily starting from the day before transplantation. Orthotopic transplantation was performed as previously described with modifications[2]. Briefly, regenerated lung grafts (n=3 for HUVEC-hMSC regenerated lungs and n=3 for hiPSC regenerated lungs) were flushed with 100 ml of ice-cold heparinized (10 units/ml) PBS under 20 mmHg right before transplantation. The regenerated left lung was dissected, the left main bronchus was ligated, and 16 G cuffs were placed in the left main PA and PV. Recipient rats were placed on a heating pad in right lateral decubitus position, anesthetized with 5% isoflurane (Abbott), intubated with a 16G endotracheal tube (Becton-Dickinson), and ventilated with a rodent ventilator (Harvard Apparatus) supplying 100% O2 (Airgas). Systemic heparinization was performed through subcutaneous injection. After left anterior thoracotomy, the left main bronchus was identified, ligated, and incised on the distal side of ligation. The left main PA and PV were identified, dissected circumferentially and incised close to the left hilum. The pulmonary arterial and venous cuffs were inserted into recipient's vessels, and secured with 7-0 silk sutures (Ethicon). Enoxaparin (2 mg/kg, NOVAPULS) was administered subcutaneously 2 hours after transplantation and then twice a day. 3 days after transplantation, recipient rats were euthanized, and the regenerated grafts were dissected out. Perfusability of the grafts was analyzed by fluorescence microangiography.

Results

Figure 7F:
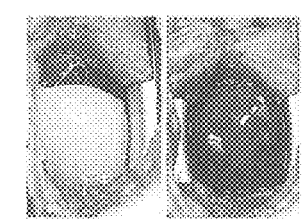
FIG. 7F is a diagram showing the procedure of the IVP-BAL assay.

A non-invasive method to assess vascular functions of regenerated lungs during isolated organ culture was performed using serial bronchoalveolar lavages (BAL) to study the perfusability and barrier function of regenerated lungs. 500-kDa dextran has been used as a tracer to study lung microvascular water permeability and vascular perfusability, and its extravasation indicates macromolecular leakage. A FITC-conjugated 500-kDa dextran was used as the tracer for in vitro lung perfusion to evaluate the pulmonary vascular perfusability and leakage before and after decellularization, and to evaluate the potential changes after re-endothelialization of acellular scaffolds. A dextran solution was perfused through the PA under 20 mmHg, and then 5 ml of blank perfusate was administered into the trachea to collect dextran leaked into the airway compartment (FIG. 7F). The total amount of dextran drained from the PV, trachea (including BAL) and lung periphery was then quantified by measuring fluorescence intensity and volume.

As a proof-of-principle, this in vitro perfusion and BAL assay were performed on freshly isolated cadaveric lungs, on lungs after exposure to 6-hour cold ischemia and on acellular lungs. Cadaveric lungs retained 100.0%±0.0% of dextran within the vascular compartment, while that of acellular lungs was 10.0%±8.0% ($p<0.01$, compared to cadaveric lungs) (FIG. 7G), which was expected, because barrier function to dextran is dependent on viable, and functional endothelium, while it diffuses across denuded vascular basement membrane over time during constant perfusion. Lungs after 6-hour cold ischemia showed compromised barrier function and a dextran retention of 87.0%±5.4%, which was significantly lower than that of cadaveric lungs ($p<0.05$) and significantly higher than that of acellular lungs ($p<0.01$) (FIG. 7G). Next, the in vitro perfusion and BAL assay were performed on HUVEC-hMSC regenerated lungs at 3 different time points (day 3, 6 and 8) during the two-phase in vitro culture. Dextran retention of HUVEC-hMSC regenerated lungs gradually increased over the culture period from 52.8%±4.2% on day 3, 75.9±3.1% on day 6, to 80.2%±5.3% on day 8 (FIG. 7H). The dextran retention in HUVEC-hMSC regenerated lungs at the end of culture was significantly higher than that of acellular lungs ($p<0.01$), significantly lower than that of cadaveric lungs ($p<0.05$), and slightly lower than but not significantly different from that of lungs after 6-hour cold ischemia ($p=0.16$). Increase of dextran retention within vascular compartment over the observed culture indicated improving barrier function with vascular maturation.

In parallel to improving barrier function, a steady decrease in vascular resistance during culture occurred. For example, daily PA pressure monitoring under constant rate perfusion (4 ml/min) revealed steady decrease of PA pressure over the culture period and reached 48.2%±15.0% at the end of culture compared to that on day 1 ($p<0.05$) (FIG. 7I). As a marker of global graft fluid homeostasis, a wet to dry ratio at the end of isolated organ culture was measured. The wet/dry ratio of regenerated lungs was 26.6±1.9, which was significantly lower than that of acellular lungs (55.7±7.9, $p<0.05$) and significantly higher than that of cadaveric lungs (9.2±0.2, $p<0.01$) and lungs after 6-hour cold ischemia (12.8±2.0, $p<0.01$) (FIG. 7J). This can be explained by the fact that pulmonary fluid balance depends on endothelial, interstitial, and epithelial functions such as active absorption of intra-alveolar fluid, and removal of interstitial fluid via lymphatics[26,27]. In the present experiment, only one of the active components, the endothelium was regenerated.

In another experiment, the HUVEC-hMSC regenerated left lungs were transplanted into Sprague-Dawley rats in orthotopic position with immunosuppression. Homogenous blood perfusion throughout the regenerated grafts can be observed right after re-perfusion (FIG. 7K). Pulmonary vessels remained perfusable at 3 days after transplantation as confirmed by fluorescence microangiography (FIG. 7L).

Example 5

Deriving Clinically Relevant Endothelial and Perivascular Cells and their Use for Pulmonary Vascular Regeneration in Small Animal Models The purpose of this example is to demonstrate a scalable cell differentiation protocol based on two-dimensional culture. The exemplary scalable cell differentiation protocol incorporates Wnt activation with CHIR99021 during pre-differentiation, TGF-β inhibition with SB431542 at the end of differentiation and hypoxic culture during the entire differentiation. Hypoxic culture condition is defined as 4% O2 in the incubator where cells are cultured.

Methods—Deriving Clinically Relevant Endothelial and Perivascular Cells

Endothelial and perivascular cell differentiation was performed under low (4%) oxygen. On Day −2, BJRiPS cells were dissociated into single cells by accutase (STEMCELL Technologies), resuspended in mTeSR™1 with 10 µM Rock inhibitor (Y-27632, Cayman Chemical), and seeded onto 6-well plates coated with Collagen IV (BD Biosciences) at 200,000 cells/well. On Day −1, BJRiPS cells were treated with CHIR99021 (12 µM, Stemgent) in mTeSR™1 for 24 hr. Starting from Day 0, BJRiPS cells were differentiated in complete differentiation medium with medium changed every other day. Complete differentiation medium was IMDM (Gibco) supplemented with 20% BIT 9500 (STEMCELL Technologies), monothioglycerol (450 µM, Sigma Aldrich), 1% MEM Non-Essential Amino Acids (Gibco), 1% GlutaMAX, 1% P/S, recombinant human BMP4 (50 ng/ml, PeproTech), VEGF (50 ng/ml, PeproTech) and bFGF (50 ng/ml, PeproTech)[1]. From Day 4 to Day 6, complete differentiation medium was further supplemented with SB431542 (10 µM, Stemgent).

On Day 6 of differentiation, cells were dissociated to single cells using TrypLE (Gibco), stained with human CD31-BV605 and CD140b-PE antibodies (BD Biosciences) or proper isotype controls, and separated by fluorescence-activated cell sorting (FACS) using FACSAriaII (BD Biosciences). BJRiPS-derived endothelial cells (hiPSC-ECs) were defined as CD31$^+$CD140b$^−$ population and BJRiPS-derived perivascular progenitor cells (hiPSC-PPCs) were defined as CD31$^−$CD140b$^+$ population. After FACS isolation, hiPSC-ECs and hiPSC-PPCs were cultured in Collagen I (BD Biosciences)-coated flasks using EGM-FBS-SB medium, which is EGM-2 without hydrocortisone, supplemented with 20% defined FBS (Hyclone), SB431542 (10 µM) and 1% P/S. For differentiation towards smooth muscle cell-like phenotype, hiPSC-PPCs were cultured in Smooth Muscle Growth Medium-2 (SmGm2, Lonza) for 6 days.

For generating growth curves of hiPSC-ECs, 150,000 hiPSC-ECs was seeded onto Collagen I-coated T75 flasks in triplicates, and cultured in EGM-FBS-SB medium. During each cell passaging, the cell number of each flask was counted and 150,000 hiPSC-ECs were seeded for the next passage.

Results—Deriving Clinically Relevant Endothelial and Perivascular Cells

Figure 9A:
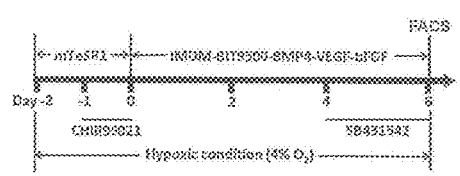
FIG. 9A is a graph showing endothelial and perivascular cell differentiation from hiPSCs. (a) A diagram showing the general procedure of endothelial and perivascular cell differentiation from hiPSCs.
Figure 9B:
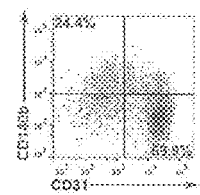
FIG. 9B is a graph showing a representative flow cytometry analysis of CD31 and CD140b expression at the end of differentiation. Two main cell populations can be observed: $CD31^+CD140b^-$ endothelial cells (hiPSC-ECs, blue) and $CD31^-CD140b^+$ perivascular progenitor cells (hiPSC-PPCs, green).
Figure 9C:
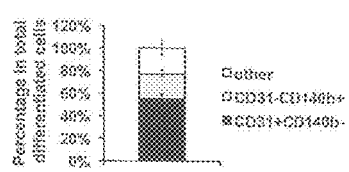
FIG. 9C is a graph showing a quantification of $CD31^+$ $CD140b^-$ hiPSC-ECs and $CD31^-CD140b^+$hiPSC-PPCs from the entire differentiation. Error bars represented standard deviations of experimental values.
Figure 9D:
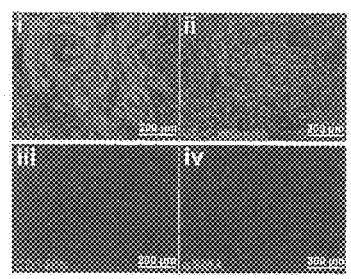
FIG. 9D is a series of images characterizing hiPSC-ECs showing homogenous expression of endothelial markers, CD31 (i, red) and VE-cadherin (ii, red), and absence of perivascular marker CD140b (iii, red) and smooth muscle marker α-SMA (iv, red) expression.

In adult lungs, CD31 and CD140b mark endothelial cells and pericytes, respectively. The differentiated cells were assayed for the expression of both markers by flow cytometry. At the end of differentiation, the resulting cell mixture was composed of two main cell types: $CD31^+CD140b^-$ endothelial cells (hiPSC-ECs, 55.1%±4.2%) and $CD31^-CD140b^+$ perivascular progenitor cells (hiPSC-PPCs, 22.1%±2.9%). These two vascular cell types constituted 77.2%±6.3% of the entire differentiation (FIG. 9B, C), demonstrating the high efficiency and specificity of this differentiation towards vascular cell types. hiPSC-ECs homogeneously expressed endothelial markers (CD31, VE-cadherin and KDR) but not the perivascular marker (CD140b), smooth muscle marker ($\alpha$-smooth muscle actin, $\alpha$-SMA) or hematopoietic marker (CD45) (FIG. 9D and FIG. 10A-C).

Figure 9E:
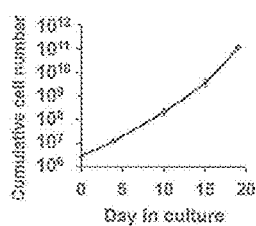
FIG. 9E is a graph showing a growth curve of hiPSC-ECs during in vitro expansion using EGM-FBS-SB medium.

An FBS-supplemented EGM-2 medium has been shown to support the expansion of human blood-derived endothelial progenitors. (Melero-Martin et al. In vivo vasculogenic potential of human blood-derived endothelial progenitor cells. *Blood* 109, 4761-4768 (2007)). SB431542 has been shown to improve in vitro expansion of human embryonic stem cell-derived endothelial cells. (James et al., Expansion and maintenance of human embryonic stem cell-derived endothelial cells by TGFbeta inhibition is Id1 dependent. Nat Biotechnol. 28, 161-166 (2010)). Human lungs are predicated to contain 220 billion cells, 30% of which are capillary endothelial cells. Herein, the medium described combines both 20% FBS and SB431542 as supplements to EGM-2 (referred to as EGM-FBS-SB medium). This EGM-FBS-SB medium allowed efficient expansion of purified hiPSC-ECs to a level sufficient for engineering human-sized lungs (FIG. 9E).

Figure 9F:
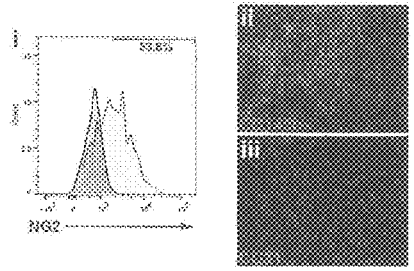
FIG. 9F is a graph and image series characterizing hiPSC-PPCs showing that more than half of the cells expressed pericyte marker NG2 (i), homogenous expression of CD140b (ii, red), and absence of endothelial marker CD31 (iii, red) expression.

By the end of expansion, hiPSC-ECs maintained homogenous expression of endothelial markers. Purified hiPSC-PPCs homogenously expressed CD140b but not endothelial CD31. More than half of hiPSC-PPCs also expressed pericyte marker, NG2 (FIG. 9F).

Figure 9G:
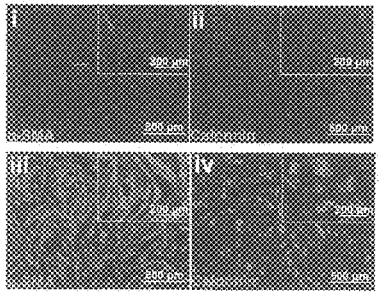
FIG. 9G is a series of images showing a smooth muscle differentiation of hiPSC-PPCs. When cultured in EGM-FBS-SB medium, hiPSC-PPCs expressed low levels of smooth muscle markers, α-SMA (i, green) and Calponin (ii, green). After 6-day differentiation in SmGm-2, α-SMA (iii, green) and Calponin (iv, green) expression was highly elevated.
Figure 9H:
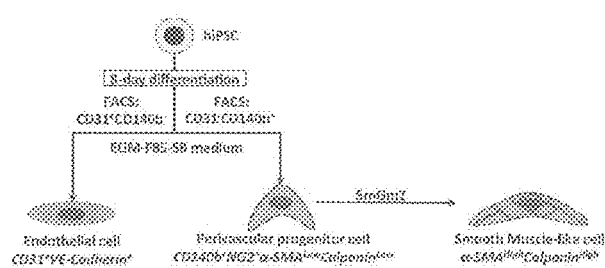
FIG. 9H is a diagram summarizing hiPSC-EC and hiPSC-PPC differentiation from hiPSCs and further differentiation of hiPSC-PPCs toward smooth muscle-like cells.
Figure 10A:
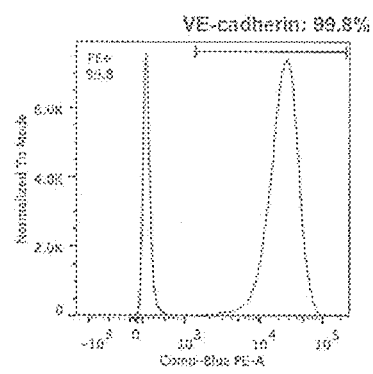
FIGS. 10A-C are graphs showing a flow cytometry analysis of VE-cadherin (a), KDR (b) and CD45 (c) in purified hiPSC-ECs, demonstrating homogenous expression of endothelial marker (VE-cadherin and KDR) and absence of hematopoietic marker CD45 expression.
Figure 10B:
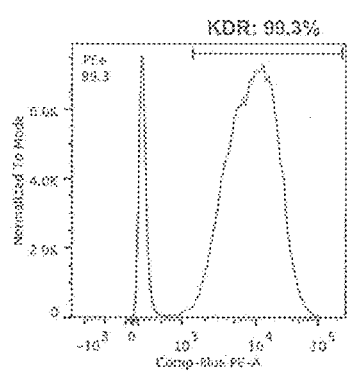
Figure 10C:
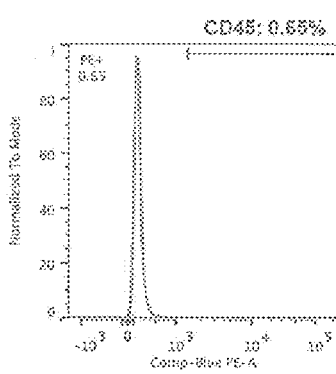

Pericytes are multipotent cells with plasticity to become smooth muscle cells and other mesenchymal cells, which has been observed during in vivo vascular remodeling and in vitro differentiation. To show this potential, smooth muscle differentiation was induced in hiPSC-PPCs by switching the culture medium to Smooth Muscle Growth Medium-2 (SmGm-2). When cultured in expansion medium (EGM-FBS-SB) for days to weeks depending on the target number of expanded cells, hiPSC-PPCs remained proliferative and expressed low level of smooth muscle markers ($\alpha$-SMA and Calponin). The culture period can range from a few days to a few weeks depending on the target number of cells to be achieved from the expansion. After culturing in SmGm-2 for 6 days, hiPSC-PPCs became less proliferative and expressed high level of $\alpha$-SMA and Calponin (FIG. 9G, H).

Methods—Two-Phase Culture of an Acellular Rat Lung Lobe Regenerated with hiPSC-ECs and hiPSC-PPCs 40 million hiPSC-ECs were mixed with 20 million mCherry-labeled hiPSC-PPCs and seeded into acellular lung scaffolds from both the PA and PV as described above. After 2 hours static culture, perfusion was re-initiated at 1 ml/min from both the PA and PV. Starting from day 1, PV cannula was released, and perfusion was switched to 4 ml/min from the PA only, which remained until the end of culture. hiPSC regenerated lungs were cultured in angiogenic medium supplemented with phorbol-12-myristate-13-acetate (PMA, 50 ng/ml, Cell Signaling Technology) during the initial 4 days, and then cultured in stabilization medium for additional 2 days. hiPSC regenerated lungs were harvested for functional and histological assessment on day 6.

To regenerate pulmonary vasculature using hiPSC-derived cells, acellular rat lungs were co-seeded with hiPSC-ECs and PPCs, and culturing these hiPSC-regenerated lungs sequentially under continuous perfusion with angiogenic media for 4 days and in stabilizing for additional 2 days. Phorbol 12-myristate 13-acetate (PMA) has been shown to facilitate efficient vascular remodeling, and, therefore, the angiogenic medium was supplemented with PMA for hiPSC regenerated lung culture to promote endothelial survival and vascular remodeling.

Figure 11A:
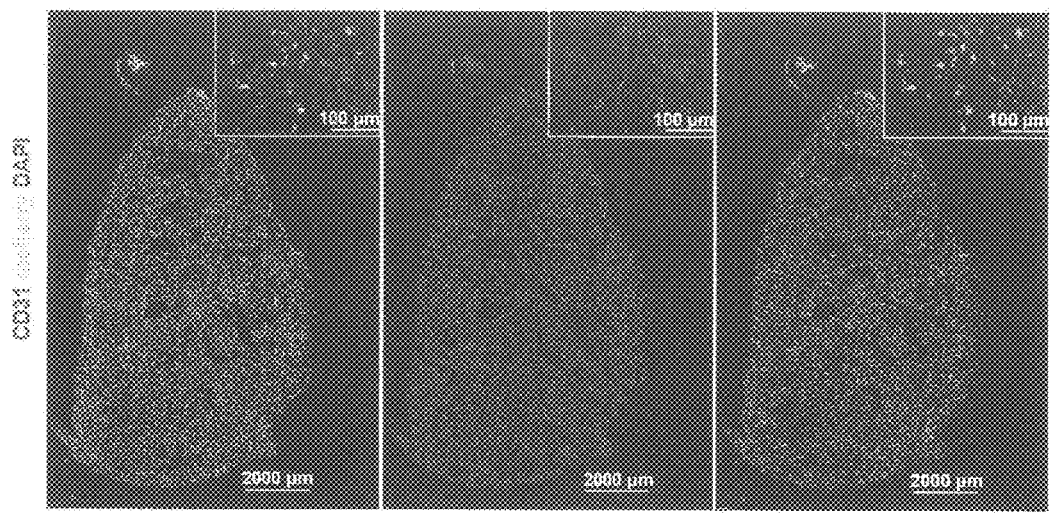
FIG. 11A is a representative stitched image of a hiPSC regenerated lung lobe after two-phase culture (CD31, purple; mCherry, yellow; DAPI, blue).
Figure 11B:
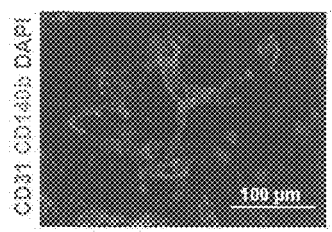
FIG. 11B is an image showing of the presence of individual hiPSC-PPCs (CD140b, green) adhering to endothelial networks formed by hiPSC-ECs (CD31, purple).
Figure 11C:
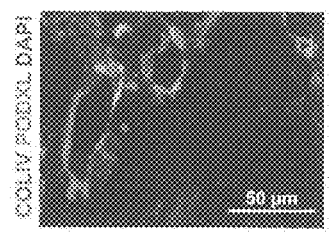
FIG. 11C is an image showing the establishment of apical-basal polarity shown by localization of PODXL (green) on the luminal surface and ColIV (red) on the basement surface.
Figure 11D:
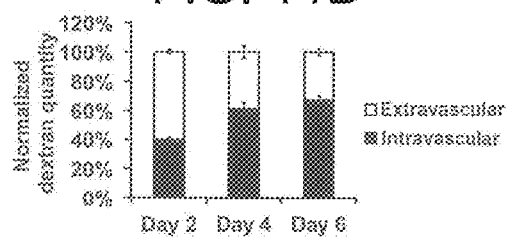
FIG. 11D is a graph showing a quantification of dextran quantities in the vascular and non-vascular compartments after the in vitro perfusion and BAL assay on hiPSC regenerated lungs on day 2, 4, and 6 of culture.
Figure 11E:
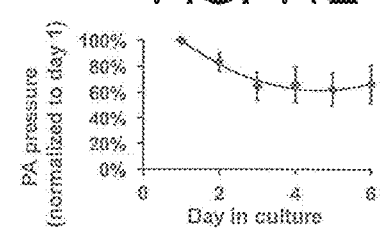
FIG. 11E is a graph showing daily PA pressure measurement of hiPSC regenerated lungs (normalized to the pressure values on day 1).
Figure 11F:
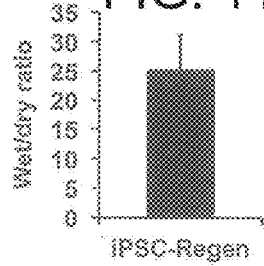
FIG. 11F is a graph showing the wet/dry ratio of accessory lobes from hiPSC regenerated lungs at the end of two-phase culture (iPSC-Regen).
Figure 11G:
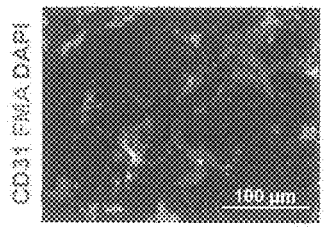
FIG. 11G is an image showing fluorescence microangiography (FMA) of hiPSC regenerated left lung grafts 3 days after transplantation, showing 0.2-µm microspheres (FMA, green) perfused through the regenerated vascular network (CD31, purple).

Results: Two-Phase Culture of an Acellular Rat Lung Lobe Regenerated with hiPSC-ECs and hiPSC-PPCs By the end of culture, a viable endothelial network was present throughout the entire lung. Additionally, the homing of hiPSC-PPCs into perivascular spaces was confirmed by both transgenic mCherry labeling and CD140b expression (FIG. 11A, B). Physiological apical-basal polarity was re-established in hiPSC regenerated lungs, indicating vascular lumen formation using hiPSC-derived vascular cells (FIG. 11C). Similar to the functional readout in HUVEC-hMSC regenerated lungs, dextran retention in hiPSC-regenerated lungs gradually increased over the culture period, reaching 39.6%±1.2% on day 2, 61.2%±4.2% on day 4 and 67.3%±2.5% on day 6 (FIG. 11D). Daily PA pressure monitoring indicated steady decrease of PA pressure during the initial 3 days of culture reaching 64.8%±10.6% on day 3 compared to day 1, which remained stable thereafter (FIG. 11E). Wet/dry ratio of hiPSC-regenerated lungs was 25.1±6.1 (FIG. 11F), which was not significantly different from that of HUVEC-hMSC regenerated lungs (p=0.83). Perfusable vessels within hiPSC-regenerated left lungs can be detected at 3 days after orthotopic transplantation as indicated by fluorescence microangiography (FIG. 11G).

In summary, the pulmonary vasculature was regenerated based on acellular rat lungs using hiPSC-derived vascular cells, and achieved similar morphological and functional milestones as those achieved using primary human endothelial and perivascular cells.

Example 6

Regenerating Pulmonary Vasculature of Human Scale and Assessing Functionality of Lung Tissue The purpose of this example is to demonstrate the ability to regenerate pulmonary vasculature of human scale and assess functionality of lung tissue. The scalable cell differentiation protocol incorporates Wnt activation with CHIR99021 during pre-differentiation, TGF-$\beta$ inhibition with SB431542 at the end of differentiation and hypoxic culture during the entire differentiation Methods—Two-Phase Culture of an Acellular Human Lung Lobe Regenerated with hiPSC-ECs and hiPSC-PPCs The right upper lobe of a decellularized human lung was dissected, and both the main PA and PV were cannulated using barbed luer adapters (Cole-Parmer). The acellular human lung lobe was primed by perfusing with 1 L Hank's balanced salt solution with human Fibronectin (2.5 $\mu$g/ml) at 10 ml/min from both the PA and PV for 1 hour, followed by washing in Hank's balanced salt solution and equilibration in medium. 282 million hiPSC-ECs and 125 million mCherry-labeled hiPSC-PPCs were mix and resuspended in 1 L of medium, and separated into two seeding chambers (each with 500 ml of cell suspension). Cells were seeded under a gravity equal to 50 mmHg simultaneously from both the PA and PV. After 2 hours static culture, perfusion was re-initiated at 10 ml/min from both the PA and PV. The hiPSC regenerated human lung lobe was cultured in angiogenic medium (containing PMA, 50 ng/ml) during the initial 4 days, and then cultured in stabilization medium for additional 2 days. The hiPSC regenerated human lung lobe was harvested for functional and histological assessment on day 6.

Methods—Resazurin Perfusion in the Regenerated Human Lung

To visualize viable cells in the hiPSC regenerated human lung lobe, resazurin perfusion was performed on day 6 of culture. Briefly, 40 ml of PrestoBlue reagent (Molecular Probes) was diluted in about 1.5 L of culture medium, and perfused through the regenerated human lung lobe at 10 ml/min from both the PA and PV for 2 hr.

Results—Resazurin Perfusion in the Regenerated Human Lung

The methodologies described herein using a rodent model was upscaled to regenerating the pulmonary vasculature of human-sized lungs. For example, a mixture of 282 million hiPSC-ECs and 125 million hiPSC-PPCs generated as described above was delivered into the main PA and PV of an acellular human lung lobe (FIG. 12A, B). The re-seeded human lung lobe was cultured in angiogenic medium (containing PMA) for 4 days and then in stabilization medium for additional 2 days. To visualize the general distribution of vascular cells throughout the entire lobe and evaluate their viability, a resazurin perfusion assay was developed. Resazurin-based reagent turns red when gets metabolized by live cells, and therefore indicates distribution of viable cells. After 2 hours of resazurin perfusion, an estimate of more than 60% of the regenerated human lung lobe was highlighted by red indicating cellularization (FIG. 12B-iv). This was confirmed by histological analysis at the end of culture showing optimal endothelial distribution similar to that achieved in rat lung regeneration (FIG. 12C). The close association of hiPSC-PPCs around the vascular network was also recapitulated in the regenerated human lung lobe shown by both transgenic mCherry labeling and CD140b staining (FIG. 12D). Vascular lumen structures can be readily detected (FIG. 12C), and their perfusability was demonstrated by fluorescence microangiography (FIG. 12E). In summary, the cell delivery and organ culture strategies described herein and based on acellular rat lungs can be upscaled to regenerate the human lung vasculature using hiPSC-derived cells.

OTHER EMBODIMENTS

It is to be understood that while the invention has been described in conjunction with the detailed description thereof, the foregoing description is intended to illustrate and not limit the scope of the invention. It will be understood that various modifications may be made without departing from the spirit and scope of the invention. Accordingly, other embodiments are within the scope of the following claims.

What is claimed is:

1. A method for vascular regeneration, comprising:
   (a) delivering endothelial cells to a lung scaffold;
   (b) delivering perivascular cells to the lung scaffold;
   (c) providing a multiphase culture program to the scaffold, the multiphase culture program comprising:
       (1) a first phase including delivering a first medium having 40-100 ng/ml of pro-angiogenic factors, and
       (2) a second phase including delivering a second medium having 0.5-2% of serum and 1-20 ng/ml of pro-angiogenic factors, forskolin, and hydrocortisone, the second medium configured to promote vascular stabilization and barrier function functionality.

2. The method of claim 1, wherein the pro-angiogenic factors include at least one of recombinant human vascular endothelia growth factor, basic fibroblast growth factor, angiopoietin 1, epidermal growth factor, and platelet-derived growth factor (VEGF, bFGF, ANG1, EGF and PDGF).

3. The method of claim 1, wherein providing the multiphase culture program to the scaffold comprises culturing totally for 8 days and, wherein the first phase comprises culturing in the first medium for 6 days and wherein the second phase comprises culturing in the second medium for 2 days.

4. A method for vascular regeneration comprising:
   (a) delivering human umbilical vein endothelial cells (HUVECs) and perivascular supporting human mesenchymal stem cells (hMSCs) to a lung scaffold;
   (b) delivering a first medium comprising pro-angiogenic factors to the lung scaffold during a first phase; and
   (c) delivering a second medium configured to promote vascular stabilization and barrier function functionality to the lung scaffold during a second phase, wherein the second medium comprises pro-angiogenic factors provided at lower levels with respect to the first medium, and wherein the second medium comprises forskolin and hydrocortisone.

5. The method of claim 4, further comprising maintaining the lung scaffold in a bioreactor surrounding the lung scaffold, the bioreactor comprising a tracheal line, an arterial line, and a venous line.

6. The method of claim 4, further comprising culturing the human umbilical vein endothelial cells (HUVECs) and the perivascular supporting human mesenchymal stem cells (hMSCs) delivered to the lung scaffold in the first medium for 6 days and in the second medium for 2 days.

\* \* \* \* \*